US006656714B2

(12) United States Patent
Holmes et al.

(10) Patent No.: US 6,656,714 B2
(45) Date of Patent: Dec. 2, 2003

(54) NUCLEIC ACIDS AND PROTEINS OF A RAT GANGLIOSIDE $GM_1$-SPECIFIC $\alpha 1 \rightarrow 2$ FUCOSYLTRANSFERASE AND USES THEREOF

(75) Inventors: Eric H. Holmes, Bothell, WA (US); Anne L. Sherwood, Mountlake Terrace, WA (US)

(73) Assignee: Northwest Hospital, Seattle, WA (US)

( * ) Notice: Subject to any disclaimer, the term of this patent is extended or adjusted under 35 U.S.C. 154(b) by 163 days.

(21) Appl. No.: 09/999,672

(22) Filed: Oct. 31, 2001

(65) Prior Publication Data

US 2002/0127655 A1 Sep. 12, 2002

Related U.S. Application Data

(62) Division of application No. 09/298,886, filed on Apr. 23, 1999, now Pat. No. 6,329,170.

(51) Int. Cl.[7] .......................... C12N 9/00; C12N 15/00; C12N 5/00; C12P 21/04; C07K 1/00; C07H 21/04
(52) U.S. Cl. ..................... 435/183; 435/69.1; 435/69.7; 435/320.1; 435/325; 435/243; 530/350; 536/23.1; 536/23.2; 536/23.5
(58) Field of Search ........................... 435/69.1, 320.1, 435/325, 455, 243, 183, 69.7; 536/23.1, 23.5, 23.2; 530/350

(56) References Cited

PUBLICATIONS

Baumann, et al., "Neutral Fucolipids and Fucogangliosides of Rat Hepatoma HTC and H35 Cells, Rat Liver, and Hepatocytes," *Cancer Research* 39: 2637–2643 (1979).
Holmes & Hakomori, "Isolation and Characterization of a New Fucoganglioside Accumulated in Precancerous Rat Liver and in Rat Hepatoma Induced by N–2–Acetylaminofluorene," *J. Biol. Chem.* 257: 7698–7703 (1982).
Holmes & Hakomori, "Enzymatic Basis for Changes in Fucoganglioside during Chemical Carcinogenesis," *J. Biol. Chem.* 258: 3706–3713 (1983).
Scribner, et al., "Use of 2–Acetamidophenanthrene and 2–Acetamidofluorene in Investigations of Mechanisms of Hepatocarcinogenesis," *Environ. Health Perspect.* 49: 81–86 (1983).
Nilsson, et al., "Fucosyl–$G_{M1}$—A Ganglioside Associated With Small Cell Lung Carcinomas," *Glycoconjugate J.* 1: 43–49 (1984).
Fredman, et al., "Binding Specificity of Monoclonal Antibodies to Ganglioside, Fuc–$G_{M1}$," *Biochim. Biophys. Acta* 875: 316–323 (1986).
Holmes & Hakomori, "The Chemical Carcinogen–Induced Enzyme, GDP–Fucose: $GM_1$ $\alpha 1 \rightarrow 2$ Fucosyltranferese in Rat Liver and Hepatoma: Modulation by and Association with Phospholipids," *J. Biochem.* 101: 1095–1105 (1987).

Hakomori, "Aberrant Glycosylation in Tumors and Tumor–Associated Carbohydrate Antigens," *Adv. Cancer Res.* 52: 257–331 (1989).
Kusunoki, et al., "Discrimination of Human Dorsal Root Ganglion Cells by Anti–fucosyl GM1 Antibody," *Brain Res.* 494: 391–395 (1989).
Holmes, "GDP–fucose: $GM_1$ $\alpha 1 \rightarrow 2$fucosyltransferase is Activated in Parenchymal Cells of Rat Liver During Early Stages of N–2–acetylaminofluorene Induced Hepatocarcinogenesis," *Carcingenesis* 11: 89–94 (1990).
Larsen, et al., "Molecular Cloning, Sequence, and Expression of a Human GDP–L–fucose: β–D–galactoside 2–α–L–fucosyltransferase cDNA that can Form the H Blood Group Antigen," *Proc. Natl. Acad. Sci. USA* 87:6674–6678 (1990).
Kusunoki, et al., "Developmental Changes of Fucosylated Glycoconjugates in Rabbit Dorsal Root Ganglia," *Neurosci. Res.* 15: 74–80 (1992).
Henion, et al., "Defining the Minimal Size of Catalytically Active Primate $\alpha 1,3$ Galactosyltransferase: Structure— Function Studies on the Recombinant Truncated Enzyme," *Glycobiology* 4: 193–201 (1994).
Piau, et al., "Evidence of Two Distinct $\alpha(1,2)$–fucosyltransferase Genes Differentially Expressed Throughout the Rat Colon," *Biochem. J.* 300: 623–626 (1994).
Hitoshi, et al., "Molecular Cloning and Expression of Two Types of Rabbit β–Galactoside $\alpha 1,2$–Fucosyltransferase," *J. Biol. Chem.* 270: 8844–8850 (1995).
Holmes, et al., "Structure–Function Analysis of Human $\alpha 1 \rightarrow 3$Fucosyltransferases," *J. Biol. Chem.* 270: 8145–8151 (1995).
Kelly, et al., "Sequence and Expression of a Candidate for the Human Secretor Blood Group $\alpha(1,2)$ Fucosyltransferase Gene (FUT2)," *J. Biol. Chem.* 270: 4640–4649 (1995).

(List continued on next page.)

*Primary Examiner*—Jeffrey Fredman
*Assistant Examiner*—Sumesh Kaushal
(74) *Attorney, Agent, or Firm*—Townsend and Townsend and Crew LLP

(57) ABSTRACT

A rat ganglioside $GM_1$-specific $\alpha 1 \rightarrow 2$fucosyltransferase is disclosed. Nucleotide sequences of a rat ganglioside $GM_1$-specific $\alpha 1 \rightarrow 2$fucosyltransferase, amino acid sequences of its encoded protein (including peptide or polypeptide), and derivatives thereof are described. Also described are fragments (and derivatives and analogs thereof) which comprise a domain of rat ganglioside $GM_1$-specific $\alpha 1 \rightarrow 2$fucosyltransferase with catalytic activity. Methods of production of rat ganglioside $GM_1$-specific $\alpha 1 \rightarrow 2$fucosyltransferase and derivatives and analogs thereof (e.g. by recombinant means) are provided. Methods of inhibiting the function of rat ganglioside $GM_1$-specific $\alpha 1 \rightarrow 2$fucosyltransferase (e.g. by means of antisense RNA) are provided. Methods of commercial scale use of the rat ganglioside $GM_1$-specific $\alpha 1 \rightarrow 2$fucosyltransferase in the production of fucosylsaccharide compositions are described. Applications of these compositions, e.g. as additives for human nutritive compositions or immunotherapeutics for cancer, are disclosed.

11 Claims, 10 Drawing Sheets

OTHER PUBLICATIONS

Figure 1:
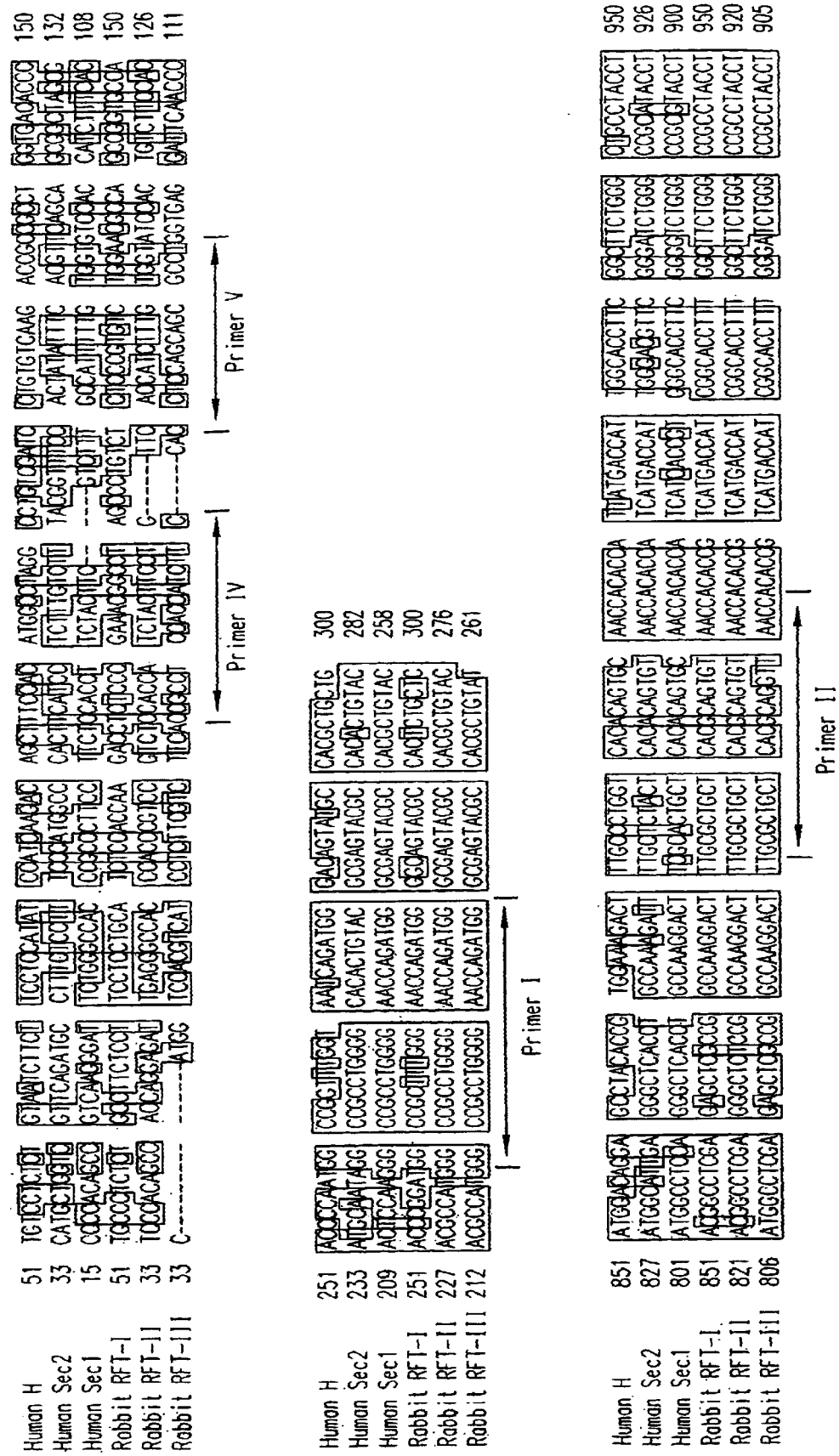

Hitoshi, et al., "Expression of the β–Galactoside α1,2–Fucosyltransferase Gene Suppresses Axonal Outgrowth of Neuro2a Neuroblastoma Cells," *J. Neurochem.* 66: 1633–1640 (1996).

Hitoshi, et al., "Molecular Cloning and Expression of a Third Type of Rabbit GDP–L–Fucose:β–D–Galactoside 2–α–L Fucosyltransferase," *J. Biol. Chem.* 271: 16975–16981 (1996).

Koda, et al., "Structure and Expression of H–type GDL–L–Fucose:β–D–Galactoside 2–α–L–Fucosyltransferase Gene (FUT1)," *J. Biol. Chem.* 272: 7501–7505 (1997).

Koda, et al., "Structure and Expression of the Gene Encoding Secretor–type Galactoside 2–α–L–fucosyltransferase (FUT2)," *Eur. J. Biochem.* 246: 750–755 (1997).

Sherwood & Holmes, "Cloning and Expression of the Catalytic Domain from Rat Hepatoma H35 Cell GDP–Fucose:$GM_1$ α1→2 Fucosyltransferase, an Enzyme Which is Activated during Early Stages of Chemical Carcinogenesis in Rat Liver," *Arch. Biochem. Biophys.* 355: 215–221 (1998).

CCTCCAGCAGCGAATAGTGAAGCTCCAACCCTGTCAGAGAAGGAATTACCGATGACGACTCAAATGTCCTCGGGAAACACAGAAAGCCCAGAGATGCGACGGACAGC
L Q Q R I V K L Q P L S E K E L P M T T Q M S S G N T E S P E M R R D S

GAGCAGCATGGAATGGAGAGCTGCCGGGGCATGTTCACGATCAATTCCATTGGCCGGCTGGGGAACCAGATGGGCGAATACCCCACACTCTTTGCACTGGCCAGGATG
E Q H G N G E L R G M F T I N S I G R L G N Q M G E Y A T L F A L A R M

AACGGACGGCTTGCGTTCATCCCGCATCCATGCACAACGCTCTACGCGCCCATCTTCAGGATCAGCCTCCCGGTGTTACACAGCGACAGGCCAAAAAGATCCCATGG
N G R L A F I P A S M H N A L A P I F R I S L P V L H S D T A K K I P W

CAGAATTACCATCTCAACGACTGGATGGAGGAGCGTTACCGCCACACCATTCCCGGACACTTTGTCCGCTTCACGGATACCGTCTGCGGGTGAATGGAGCCAGCCAGTACTTTGTC
Q N Y H L N D W M E E R Y R H I P G H F V R F T G Y P C S W T F Y H H L

CGGCCCAGAGATCCTGAAGGAGTTCACCCTGCATGACCACGTGCGGGAGGAGGCCCAGGCCTTCCTGCGGGGTCTGCGCGGGTGAATGGAGCCAGCCAGTACTTTGTC
R P E I L K E F T L H D H V R E E A Q A F L R G L R V [N] G S Q P S T F V

GGTGTCCATGTGCGCCGAGGACTATGTCCATGTCATGCCTAATGTGTGGAAGGGCGTGGTGGCTGACGCCCGGGGTTACCTGGAAAAGGCCCTGGATATGTTCCGGGCA
G V H V R R G D Y V H V M P N V W K G V V A D R G Y L E K A L D M F R A

CGCTATTCATCTCCAGTCTTCGTGGTTACAAGCAAGGGTATGGCCTGGTCCGGGAGAACATTAATGCTTCCCGAGGAGACCTGGTGTTCGCGGGCAATGGTATTGAG
R Y S S P V F V V T S N G M A W C R E N I [N] A S R G D Y V F A G N G I E

GGGTCGCCAAGGACTTCGCGCTGCTGACCCAGTGCAACCACCATCATGACTTTGGATTTGGGCTGCTCCAGTGGTGCTGATACCATC
G S P A K D F A L L T Q C [H] T I M T I G T F G I W A A Y L A G G D T I

TACTTAGGCCAACTACACCCTTCCGGATTCTCCGGTTCCTGAAGTCTTTAAGCCAGAGGCAGCCTTCCTACCCGAATGGGTGGGCATCCCTGCCGATCTGTCCCCACTC
Y L A [N] Y T L P D S P F L K V F K P E A A F L P E W V G I P A D L S P L

CTTAAGGCACATTAACCAGCCTGTCCTGCTCGGTTCACCTTGTTACGTCGCAGGAAGAGCCTTCTGATGGGAA
L K A L T P A C P R S H F H L K A K G V I C Y V A G R A F

FIG.3A

```
Rat H35 cell FucT                                     LQQRIVKLQPLSEKELPMTTQMSSGNTESPEMRRDSEQHGNGEL  44
Human Sec2         MLVVQMPFSFPMAHFILFVFTVVSTIFHVQQLAKIQAMMELPVQIPVLASTSKALGPSQL               60

Rat H35 cell FucT  RGMFTINSIGRLGNQMGEYATLFALARMNGRLAFIPASMHNALAPIFRISLPVLHSDTAK             104
                   ::: :::::::::::::::::::::::::::::::: ::::::::::: :::::
Human Sec2         RGMWTINAIGRLGNQMGEYATLYALAKMNGRPAFIPAQMHSTLAPIFRITLPVLHSATAS            120

Rat H35 cell FucT  KIPWQNYHLNDWMEERYRHIP-GHFVRFTGYPCSWTFYHHLRPEILKEFTLHDHVREEAQ            163
                   :::::::::::::::::::::  ::::::::::::::::::: ::::::::::::::::
Human Sec2         RIPWQNYHLNDWMEEEYRHIPPGEYVRFTGYPCSWTFYHHLRQEILQEFTLHDHVREEAQ           180

Rat H35 cell FucT  AFLRGLRVNGSQPSTFVGVHVRRGDYVHVMPNVMLGVVADRGYLEKALDMFRARYSSPVF           223
                   ::::::::: :: ::::::::::::::::::: :::::::::    :::::::::: :
Human Sec2         KFLRGLQVNGSRPGTFVGVHVRRGDYVHVMPKVMLGVVADRRYLQQALDMFRARYSSLIF          240

Rat H35 cell FucT  VVTSNGMAWCRENIINASRGDVVFAGNGIEGSPAKDFALLTQCNHTIMTIGTFGIWAAYLA         283
                   :::::::::::::: ::::::::::: ::::::::::::::::::::::::::::::::
Human Sec2         VVTSNGMAWCRENIDTSHGDVVFAGDGIEGSPAKDFALLTQCNHTIMTIGTFGIWAAYLA          300

Rat H35 cell FucT  GGDTIYLANYTLPDSPFLKVFKPEAAFLPEWVGIPADLSPLLKALTPACPRSHFHLKAKG         343
                   :::::::::::::::::::::: ::::::::: :::::::::
Human Sec2         GGDTIYLANYTLPDSPFLKIFKPEAAFLPEWTGIAADLSPLLKH Rat H35 cell FucT  VICYVAGRAF
```

FIG. 3B

```
ATGGCCAGCGCCCAGGTTCCCTTCTCCTTCCCTCTGGCCCACTTCCTCATCTTTGTCTTCGTGACTTCCACCATCCAC
 M  A  S  A  Q  V  P  F  S  F  P  L  A  H  F  L  I  F  V  F  V  T  S  T  I  I  H

CCTCCAGCAGCGAATGAAGCTCCAACCCTGTCAGAGGAATTACCGATGACGACTCAAATGTCCTCGGGAAACACAGAAGCCCAGAGATGCCACGGACAGC
 L  Q  Q  R  I  V  K  L  Q  P  L  S  E  K  E  L  P  M  T  T  Q  M  S  S  G  N  T  E  S  P  E  M  R  R  D  S

GAGCAGCAGGCTTGGTCATCCCGGCATGTCAGGAGCTGCGGGGCATGTTCACGATCAATTCCATTGGCCGGCTGGGGAACCAGATGGGGGAATACGCCACACTCTTTGCACTGGCCAGGATG
 E  Q  H  G  N  G  E  L  R  G  M  F  T  I  N  S  I  G  R  L  G  N  Q  M  G  E  Y  A  T  L  F  A  L  A  R  M

AACGGACGCCTTGCGTTCATCCCGGCATCAATGCACAATGCTCTAGCGCCCATCTTCAGGATCAGCCTGCCGGTGTTACACAGCGACACGGCCAAAAAGATCCCATGG
 N  G  R  L  A  F  I  P  A  S  M  H  N  A  L  A  P  I  F  R  I  S  L  P  V  L  H  S  D  T  A  K  K  I  P  W

CAGAATTACCATCTCAACGACTGGATGGAGGAGCGTTACCGCCACATTCCGGGACACTTCGTGCGCTTCACGGGATACCGTGCTCTGAGGGGATACCCGAGTACTTTGTG
 Q  N  Y  H  L  N  D  W  M  E  E  R  Y  R  H  I  P  G  H  F  V  R  F  T  G  Y  P  C  S  W  T  F  Y  H  H  L

CGCCCAGAGATCCTGAAGGAGTTCACCCTGCACGACCACGTCCGAGAGGAGGCCCAGGCCTTCCTGCGGGGTCTGCGTGTTGACGCGGGTTACCTGGAGAAAGGCCCTGAATATGTTCCGGGCA
 R  P  E  I  L  K  E  F  T  L  H  D  H  V  R  E  E  A  Q  A  F  L  R  G  L  R  V  N  G  S  Q  P  S  T  F  V

GGTGTCCATGTGCGGCGAGGGGACTATGTCCATGTCATGCCTAATGTGCATGGTGAAGGGCGTGGTGCCTGAGGAGAACATTAATGCTTCCGAGGAGACGGTGTGTTGCGCGGCAATGGTATTGAG
 G  V  H  V  R  R  G  D  Y  V  H  V  M  P  N  V  W  K  G  V  V  A  D  R  G  Y  L  E  K  A  L  D  M  F  R  A

CGGCTATTCATCATCCGGAGGGACTCTTCGTGGTTGTGGGTTACAAGCAACGGTATGGCCAGCAACCACCATCATGACTATTGGGACCTTTGGGATTGGCCGCTCGCCAGTGGTGATACCATC
 R  Y  S  S  P  V  F  V  V  T  S  N  G  M  A  W  C  R  E  N  I  N  A  S  R  G  D  V  V  F  A  G  N  G  I  E

GGGTGGCCACCAGGCCAAGGACTTCGCGCTTCGGCCAAGTCTCCGGATTCCAACAGTGCAGCCCTCATTCTTCAAAGTCTTCAAGCCAGAGGCAGCCTTCCTACCGGAATGGGTGGCATCGCCGATCGTCCCCACTC
 G  S  P  A  K  D  F  A  L  L  T  Q  C  N  H  T  I  M  T  I  G  T  F  G  I  W  A  A  Y  L  A  G  G  D  T  I

TACTTAGCCAACTACACCCTTCCTGACTCCCCGTTCCTCAAAGTCTTTAAGCCAGAGGCAGCCTTTCTCCCAGAATGGGTGGCATCCCTGCCATCTGTCCCACTC
 Y  L  A  N  Y  T  L  P  D  S  P  F  L  K  V  F  K  P  E  A  A  F  L  P  E  W  V  G  I  P  A  D  L  S  P  L

CTTAAGGCATTAACACACCCTGCCTGCCCGCGTCCTCGTGTCCACTTCCACCTTCCACCTTGTTACCTCCGCAGGAAAGAGAGCCTTCACTGTTCTGTGCCTCTGATGGGAA
 L  K  A  L  T  P  A  C  P  R  S  H  F  F  H  L  K  A  K  G  V  T  C  Y  V  V  A  G  R  A  F
```

FIG. 5

|     | cpm - background | % initial activity |
|-----|------------------|--------------------|
| I   | 19,832           | 100                |
| II  | 0                | 0                  |
| III | 6,726            | 34                 |
| IV  | 4,917            | 25                 |
| V   | 1,043            | 5.3                |
| VI  | 104              | 0.52               |

NUCLEIC ACIDS AND PROTEINS OF A RAT GANGLIOSIDE $GM_1$-SPECIFIC α1→2 FUCOSYLTRANSFERASE AND USES THEREOF

The present application is a divisional application of U.S. Ser. No. 09/298,886, filed Apr. 23, 1999, now U.S. Pat. No. 6,329,170, the entire disclosure of which is hereby incorporated by reference.

This invention was made with government support under Research Grant CA70740 from the National Cancer Institute. The government has certain rights in the invention.

1. FIELD OF THE INVENTION

The present invention relates to a rat ganglioside $GM_1$-specific α1→2fucosyltransferase. The invention provides novel nucleotide sequences of a rat α1→2fucosyltransferase specific for a carbohydrate moiety found in ganglioside $GM_1$, more particularly, specific for a terminal galactose β1→3N-acetylgalactosamine (Galβ1→3GalNAc) saccharide, amino acid sequences of its encoded protein (including peptide or polypeptide), and derivatives and analogs thereof. Merely for the ease of description, the enzyme is herein referred to as "$GM_1$-specific" or "ganglioside $GM_1$-specific". The invention also relates to fragments (and derivatives and analogs thereof) which comprise a domain of rat ganglioside $GM_1$-specific α1→2fucosyltransferase with catalytic activity. Methods of production of rat ganglioside $GM_1$-specific α1→2fucosyltransferase and derivatives and analogs thereof (e.g. by recombinant means) are provided. In addition, the invention relates to methods of inhibiting the function of rat ganglioside $GM_1$-specific α1→2fucosyltransferase (e.g. by means of antisense RNA). The invention further relates to use of rat ganglioside $GM_1$-specific α1→2fucosyltransferase in the preparative production of fucosyl-$GM_1$. Applications of fucosyl-$GM_1$, for example as an immunotherapeutic for cancer, are disclosed.

2. BACKGROUND OF THE INVENTION

Citation of a reference herein shall not be construed as an admission that such reference is prior art to the present invention.

2.1. Fucosyltransferases

Fucosyltransferases are enzymes that catalyze the addition of a fucose residue to a terminal galactose acceptor of saccharide precursors. Fucosyltransferase activity is involved in the production of oligosaccharides, glycolipids or glycoproteins. There are four known classes of fucosyltransferases, namely those that catalyze the addition of fucose in α1→2, α1→3, α1→4 and α1→6 linkages.

Fucosyltransferases are best known for their roles in the synthesis of the oligosaccharide moieties that comprise blood group antigenic determinants. For example, the fucosyltransferase encoded by the H gene catalyzes the transfer of fucose in an α1→2 linkage to the terminal galactose of Gal(β1→4)GlcNAc(β1-3)Gal-R to produce 'H substance' on the surface of erythrocytes. Further addition of N-acetylgalactosamine or galactose leads to the formation of the type A or type B blood group substances respectively. An analogous enzyme encoded by the Se locus catalyzes the formation of 'H substance' in epithelial tissues for secretion rather than presentation at the cell surface (Rosen et al., 1989, Dictionary of Immunology, Stockton Press, New York, pp. 1–3).

Previous experiments with H35 hepatoma cell extracts demonstrated that transfer of fucose to neolacto-series acceptors occurred at a rate only 2% of that found for $GM_1$ (Holmes, E. H., et al, 1983, J. Biol. Chem. 258:3706–3713). This substrate specificity is more restricted compared to other cloned α1→2fucosyltransferases but is most closely related to secretor-type enzymes (Larsen, R. D., et al., 1990, Proc. Natl. Acad. Sci. USA 87:6674–6678; Kelly, R. J., et al., 1995, J. Biol. Chem. 270:4640–4649; Hitoshi, S., et al., 1995, J. Biol. Chem. 270:8844–8850; Hitoshi, S., et al., 1996, J. Biol. Chem. 271:16975–16981).

2.2. Structure of α1→2Fucosyltransferases

To date, a number of genes encoding H-type and Se-type α1→2fucosyltransferases have been cloned from several species of organisms. Three human α1→2fucosyltransferases (Larsen et al., 1990, Biochemistry 87:6674–6678; Koda et al., 1997, Eur. J. Biochem. 246:750–755; Kelly et al., 1995, J. Biol. Chem. 270:4640–4649), three rabbit α1→2fucosyltransferases (known as RFT-I, RFT-II and RFT-III) (Hitoshi et al., 1995, J. Biol. Chem. 270:8844–8850; Hitoshi et al., 1996, J. Biol. Chem. 271:16975–19681), and two mouse α1→2fucosyltransferases (Tsuji, 1996, GenBank accession no. Y09882; Lin et al., 1998, GenBank accession no. AF064792) have been described. Piau et al. (1994, Eur. J. Biochem. 300:623–626) disclose fragments, designated FTA and FTB, of two rat α1→2fucosyltransferases isolated from rat PROb colon adenocarcinoma cells. Piau et al. showed that antisense expression of the FTA or FTB nucleic acid fragments inhibited the endogenous α1→2fucosyltransferase activity of PROb cells with respect to the synthetic fucose acceptor phenyl β-$_D$-galactopyranoside; however the FTB fragment was not shown to be sufficient for α1→2fucosyltransferase catalytic activity, nor was the substrate specificity of the PROb α1 2fucosyltransferase activity determined.

H-type α1→2fucosyltransferases are membrane localized whereas Se-type α1→2fucosyltransferases are localized to the Golgi apparatus. Amino acid sequence alignment of membrane bound H-type α1→2fucosyltransferases reveals that, like other glycosyltransferases, there exists a homologous domain structure comprising a short intracellular N-terminal domain, a transmembrane domain, an extracellular stem region not required for enzymatic activity, and finally, the catalytic domain at the C-terminus. Generally, there is little sequence homology outside the catalytic domain.

2.3. Ganglioside $GM_1$ and its Fucosylated Derivative Fucosyl-$GM_1$

Gangliosides are cell surface constituents comprising glycosphingolipids (produced by the linking of ceramides to oligosaccharides) with sialic acid residues. Depending on the number of sialic acid residues they possess, gangliosides are known as mono-, di-, tri- or polysialogangliosides. $GM_1$ stands for ganglioside mono(sialic acid)$_1$.

Fucosyl-$GM_1$, detected by monoclonal antibodies, is found largely in the nervous system, and in particular on a subpopulation of neurons in the dorsal root ganglia and dorsal horn of the spinal cord, as well as on surrounding satellite cells surrounding the fucosyl-$GM_1$ positive neurons (Kusunoki et al., 1989, Brain Res. 494:391–395; Kusonoki et al., 1992, Neurosci. Res. 15: 74–80).

Gangliosides have long been implicated in diseased states. They are often prominent cell surface constituents of transformed cells (see Section 2.5, infra) and alterations in their metabolism give rise to diseases of the nervous system. For example, several fatal hereditary diseases are caused by lysosomal storage of gangliosides wherein the absence or deficiency of lysosomal enzymes results in the deleterious accumulation of gangliosides. The most well known of these diseases is the neurodegenerative Tay-Sachs disease, which is characterized by the accumulation of ganglioside $GM_2$. Accumulation of $GM_1$ results in $GM_1$ Gangliosidosis.

2.4. Regulation of Fucosyltransferase Expression

'H substance', the fucosylated precursor of blood group determinants, is strictly regulated temporally and spatially during vertebrate development (Fenderson et al., 1986, Dev. Biol. 114:12–21).

Dramatic changes in the expression of cell surface glycolipids are found with oncogenesis (Hakomori, 1989, Adv. Cancer Res. 52:257–331; Alhadeff, 1989, CRC Crit. Rev. Oncol./Hematol. 9:37–107). These changes frequently are oncofetal in nature in that a particular carbohydrate structure may be expressed during normal fetal development, disappear in adult tissues, and reappear in association with oncogenesis giving rise to a premalignant or malignant marker. One such example is expression of the ganglio-B determinant ($II^3NeuAcIV^3$ $\alpha GalIV^2FucGg_4$) during early stages of chemical carcinogenesis in rat liver with N-2-acetylaminofluorene (AAF) (Holmes and Hakomori, 1982, J. Biol. Chem. 257:7698–7703; Scribner et al., 1983, Environ. Health Perspect. 49:81–89). Expression of this determinant has been shown to be a property of liver parenchymal cells resulting from a carcinogenic stimulus but not hepatotoxicity (Holmes, 1990, Carcinogenesis 11:89–94). This determinant has also been shown to be developmentally regulated in rat stomach (Bonhours et al., 1987, J. Biol. Chem. 258:3706–3713). Expression of this antigen is due to the activation of an $\alpha 1\rightarrow 2$fucosyltransferase which is normally unexpressed in adult rat liver parenchymal cells. This enzyme efficiently transfers fucose onto the terminal galactose residue of a $GM_1$ precursor, producing fucosyl-$GM_1$ ($IV^3NeuAcIV^2FucGgOse_4Cer$). Fucosyl-$GM_1$ is a substrate for a constituitively expressed $\alpha 1\rightarrow 3$galactosyltransferase forming the blood group B determinant on a ganglioside core chain (Holmes and Hakomori, 1983, J. Biol. Chem. 258:3706–3713; Holmes and Hakomori, 1987, J. Biochem. 258:3706–3713). This $\alpha 1\rightarrow 3$galactosyltransferase behaves as a blood group B transferase in that it efficiently catalyzes transfer of galactose in $\alpha 1\rightarrow 3$-linkage to terminal galactose residues of $\alpha 1\rightarrow 2$fucosylated neolacto- and ganglio-series acceptors (Holmes and Hakomori, 1983, J. Biol. Chem. 258:3706–3713).

High $\alpha 1\rightarrow 2$fucosyltransferase expression is observed in rat hepatoma H35 cells (Holmes and Hakomori, 1983, J. Biol. Chem. 258:3706–3713; Holmes and Hakomori, 1987, J. Biochem. 258:3706–3713). The enzyme from H35 cells has specificity for a ganglio-series core chain. These cells accumulate large amounts of fucosyl-$GM_1$ (Baumann, H., et al., 1979, Cancer Res. 39:2637–2643). Enzymological studies indicated this enzyme was inhibited by a wide variety of detergents, an unusual property for a membrane bound glycosyltransferase (Holmes, E. H., et al, 1983, J. Biol. Chem, 258:3706–3713). This property may reflect a role for membrane phospholipids in maintaining the enzyme in an active conformation (Holmes and Hakomori, 1987, J. Biochem. 101:1095–1105). Later studies demonstrated that active enzyme could be solubilized from H35 cell membranes by 0.4% CHAPSO which bound to the affinity resin GDP-hexanolamine-Sepharose (Holmes, E. H., et al., 1987, J. Biochem. 101:1095–1105).

Further, the observation about the production by transformed cells of high levels of fucosyl-$GM_1$ as a result of $\alpha 1\rightarrow 2$fucosyltransferase activity, is not restricted to rat hepatoma cells. For example, in humans, fucosyl-$GM_1$ is associated with small cell lung carcinoma (Fredman et al., 1986, Biochim. Biophys. Acta 875:316–323; Nilsson et al., 1984, Glycoconjugate J. 1:43–49).

Generally, enzymatic oligosaccharide synthesis (including synthesis of glycolipids, glycoproteins, etc.) has been limited by the difficulty of isolation and enrichment of glycosyltransferases from natural sources. Thus, there is a need for methods to produce easily isolatable quantities of glycosyltranferases with high enzymatic activity. Such glycosyltransferases, produced, e.g. in vitro, would be useful reagents in compensating for the lack of natural resources. In particular, there is a need for methods to produce easily isolatable $GM_1$-specific $\alpha 1\rightarrow 2$fucosyltransferase. The ability to synthesize fucosyl-$GM_1$ in vitro is of particularly high value, as the ganglioside is important for the development of the mammalian nervous system. $GM_1$-specific $\alpha 1\rightarrow 2$fucosyltransferase can be used to catalyze the addition of fucose residues to terminal $Gal\beta 1\rightarrow 3GalNAc$ saccharide chains of glycoproteins, glycolipids, glycolipoproteins and oligosaccharides, producing saccharide compositions that are useful nutritional additives or bases therefor. Further, fucosyl-$GM_1$ is envisaged to be an important tool in cancer therapy and cancer diagnostics. Until the cloning and characterization of the nucleic acid and amino acid sequences of the catalytic domain and the fill length $\alpha 1\rightarrow 2$fucosyltransferase of the present invention, no $\alpha 1\rightarrow 2$fucosyltransferases with $GM_1$ specificity had been identified.

3. SUMMARY OF THE INVENTION

The present invention provides a rat ganglioside $GM_1$-specific $\alpha 1\rightarrow 2$fucosyltransferase. As indicated above, the novel nucleic acids of the invention encode an $\alpha 1\rightarrow 2$fucosyltransferase enzyme specific for a terminal $Gal\beta 1\rightarrow 3GalNAc$ saccharide found naturally in ganglioside $GM_1$. According to the present invention, the novel nucleic acids encode an $\alpha 1\rightarrow 2$fucosyltransferase enzyme specific for the terminal $Gal\beta 1\rightarrow 3GalNAc$ moiety which can be a part of a glycoprotein, a glycolipid, a glycolipoprotein or free oligosaccharide or polysaccharide molecule. Merely for ease of description, and not limitation, the enzyme is referred to herein as "$GM_1$-specific" or "ganglioside $GM_1$-specific". More particularly, the invention encompasses nucleotide sequences of a rat ganglioside $GM_1$-specific $\alpha 1\rightarrow 2$fucosyltransferase, amino acid sequences of its encoded protein (including peptide or polypeptide), and derivatives and analogs thereof. The invention further encompasses fragments (and derivatives and thereof) which comprise a domain of rat ganglioside $GM_1$-specific $\alpha 1\rightarrow 2$fucosyltransferase with catalytic activity. Methods of production of rat ganglioside $GM_1$-specific $\alpha 1\rightarrow 2$fucosyltransferase (e.g. by recombinant means), and derivatives and thereof, are provided. Methods of inhibiting the function of ganglioside $GM_1$-specific $\alpha 1\rightarrow 2$fucosyltransferase (e.g. by means of antisense RNA) are provided. The invention further encompasses methods for the use of rat ganglioside $GM_1$-specific $\alpha 1\rightarrow 2$fucosyltransferase in the production of glycoproteins, glycolipids, glycolipoproteins and free oligo- or polysaccharides. Examples of uses of these products, such as uses as nutritional additives, are provided. The methods are particularly useful as they can be used in preparative biosynthesis of these saccharide-containing compositions, and are adaptable to such synthesis in large or commercial scale production. Of particular importance is the synthesis of fucosyl-$GM_1$, which is useful as an immunotherapeutic against cancer and neurological disease.

This invention provides an isolated or purified protein comprising an amino acid sequence as depicted in FIG. 5 (SEQ ID NO:8). The invention further provides an isolated or purified protein comprising amino acids 28–380 of SEQ ID NO:8 as depicted in FIG. 3A (SEQ ID NO:10).

This invention provides an isolated or purified protein consisting of an amino acid sequence as depicted in FIG. 5 (SEQ ID NO:8).

The invention further provides an isolated or purified protein consisting of amino acids sequence numbers 28–380 of SEQ ID NO:8 as depicted in FIG. 3A (SEQ ID NO:10).

This invention provides an isolated or purified protein, the amino acid sequence of which consists of a catalytic domain defined by amino acid numbers 1–353 as depicted in FIG. 3A (SEQ ID NO: 10) or amino acid numbers 28–380 as depicted in FIG. 5 (SEQ ID NO:8).

This invention provides an isolated or purified protein, the amino acid sequence of which consists of amino acid numbers 1–380 as depicted in FIG. 5 (SEQ ID NO:8) covalently linked to at least a portion of a second protein, which second protein is not said protein defined by the amino acid sequences as depicted in FIG. 5 (SEQ ID NO:8). In another embodiment, the protein is fused by a covalent bond to at least a portion of a second protein, wherein said portion is the IgG binding domain of protein A.

This invention provides an isolated or purified protein, the amino acid sequence of which consists of amino acids numbers 28–380 as depicted in FIG. 5 (SEQ ID NO:8) or amino acids numbers 1–353 as depicted in FIG. 3A (SEQ ID NO:10) covalently linked to at least a portion of a second protein, which second protein is not said protein defined by the amino acid sequences as depicted in FIG. 5(SEQ ID NO:8). In another embodiment, the protein is fused by a covalent bond to at least a portion of a second protein, wherein said portion is the IgG binding domain of protein A.

This invention provides an isolated nucleic acid comprising a nucleotide sequence as depicted in FIG. 5 (SEQ ID NO:7).

This invention provides an isolated nucleic acid comprising a nucleotide sequence encoding an amino acid sequence as depicted in FIG. 5 (SEQ ID NO:8).

This invention provides an isolated nucleic acid comprising a nucleotide sequence as depicted in FIG. 3A (SEQ ID NO:9).

This invention provides an isolated nucleic acid comprising a nucleotide sequence encoding an amino acid sequence as depicted in FIG. 3A (SEQ ID NO:10).

This invention provides an isolated RNA molecule comprising a nucleotide sequence as depicted in FIG. 5 (SEQ ID NO:7), wherein the base U(uracil) is substituted for the base T (thymine) of said sequence.

This invention provides an isolated RNA molecule comprising a nucleotide sequence encoding an amino acid sequence as depicted in FIG. 5 (SEQ ID NO:8).

This invention provides an isolated RNA molecule comprising a nucleotide sequence as depicted in FIG. 3A (SEQ ID NO:9), wherein the base U(uracil) is substituted for the base T (thymine) of said sequence.

This invention provides an isolated RNA molecule comprising a nucleotide sequence encoding an amino acid sequence as depicted in FIG. 3A (SEQ ID NO:10).

This invention provides an isolated nucleic acid comprising a nucleotide sequence that is the reverse complement of a nucleotide sequence encoding an amino acid sequence as depicted in FIG. 5 (SEQ ID NO:8).

This invention provides an isolated nucleic acid comprising a nucleotide sequence that is the reverse complement of a nucleotide sequence encoding an amino acid sequence as depicted in FIG. 3A (SEQ ID NO:10).

This invention provides a vector comprising (a) a nucleotide sequence as depicted in FIG. 5 (SEQ ID NO:7)and (b) an origin of replication. In one embodiment, the nucleotide sequence is operably linked to a heterologous promoter.

This invention provides a vector comprising (a) a nucleotide sequence as depicted in FIG. 3A (SEQ ID NO:9)and (b) an origin of replication. In one embodiment, the nucleotide sequence is operably linked to a heterologous promoter.

This invention provides a vector comprising (a) a nucleotide sequence that is the reverse complement to all or a fragment of the nucleotide sequence as depicted in FIG. 5 (SEQ ID NO:7) and (b) an origin of replication. In one embodiment, the nucleotide sequence is operably linked to a heterologous promoter.

This invention provides a vector comprising (a) a nucleotide sequence that is the reverse complement to all or a fragment of the nucleotide sequence as depicted in FIG. 3A (SEQ ID NO:9) and (b) an origin of replication. In one embodiment, the nucleotide sequence is operably linked to a heterologous promoter.

The invention provides a vector comprising (a) a nucleotide sequence encoding an amino acid sequence as depicted in FIG. 5 (SEQ ID NO:8) and (b) an origin of replication.

The invention provides a vector comprising (a) a nucleotide sequence encoding an amino acid sequence as depicted in FIG. 3A (SEQ ID NO:10) and (b) an origin of replication.

The invention provides a recombinant cell containing a recombinant nucleic acid vector comprising a nucleotide sequence as depicted in FIG. 5 (SEQ ID NO:7). In one embodiment, the recombinant cell is a eukaryotic cell and preferably a mammalian cell.

The invention provides a recombinant cell containing a recombinant nucleic acid vector comprising a nucleotide sequence as depicted in FIG. 3A (SEQ ID NO:9). In one embodiment, the recombinant cell is a prokaryotic cell and preferably a bacterial cell.

This invention provides a method of producing a rat α1→2fucosyltransferase protein comprising: (a) culturing a recombinant cell containing a vector comprising a recombinant nucleotide sequence as depicted in FIG. 5 (SEQ ID NO:7), such that the α1→2fucosyltransferase protein, encoded by SEQ ID NO:7, is expressed by the cell; and (b) recovering the expressed protein or a cellular fraction containing said protein. In one embodiment, the invention provides the purified protein produced by the method. In another embodiment, the invention provides a cellular fraction with said protein activity.

This invention provides a method of producing a rat α1→2fucosyltransferase protein comprising: (a) culturing a recombinant cell containing a vector comprising a recombinant nucleotide sequence as depicted in FIG. 3A (SEQ ID NO:9), such that the α1→2fucosyltransferase protein, encoded by SEQ ID NO:9, is expressed by the cell; and (b) recovering the expressed protein or a cellular fraction containing said protein. In one embodiment, the invention provides the purified protein produced by the method. In another embodiment, the invention provides a cellular fraction with α1→2fucosyltransferase protein activity.

This invention provides a method of producing a rat α1→2fucosyltransferase protein comprising: (a) culturing a recombinant cell containing a vector comprising a recombinant nucleotide sequence encoding a protein sequence as depicted in FIG. 5 (SEQ ID NO:8), such that the α1→2fucosyltransferase protein, encoded by SEQ ID NO:7, is expressed by the cell; and (b) recovering the expressed protein or a cellular fraction containing said protein. In one embodiment, the invention provides the purified protein produced by the method. In another embodiment, the invention provides a cellular fraction with α1→2fucosyltransferase protein activity.

This invention provides a method of producing a rat α1→2fucosyltransferase protein comprising: (a) culturing a recombinant cell containing a vector comprising a recombinant nucleotide sequence encoding a protein sequence as depicted in FIG. 3A (SEQ ID NO:10), such that the α1→2fucosyltransferase protein, encoded by SEQ ID NO:9, is expressed by the cell; and (b) recovering the expressed protein or a cellular fraction containing said protein. In one embodiment, the invention provides the purified protein produced by the method. In another embodiment, the invention provides a cellular fraction with α1→2fucosyltransferase protein activity.

This invention provides a method for detecting the onset of liver cancer comprising the detection of the expression of a nucleotide sequence as depicted in FIG. 5 (SEQ ID NO:9) or a fragment or complement thereof.

This invention provides a method to suppress or inhibit from a cell the function of the protein of the invention, which method comprises contacting said cell with a nucleic acid comprising a nucleotide sequence that is the reverse complement of a nucleotide sequence as depicted in FIG. 5 (SEQ ID NO:7) or a fragment thereof, or as depicted in FIG. 3A (SEQ ID NO:9) or a fragment thereof, and wherein when said nucleic acid is RNA, the base T (thymine) in SEQ ID NO:7 and SEQ ID NO:9 is substituted by the base U (uracil). In one embodiment, said nucleic is contained within an adenoviral or retroviral vector. In another embodiment, the cell is a human small cell lung carcinoma cell.

The invention provides methods for the preparative synthesis of compositions comprising Fucα1→2Galβ1→3GalNAc, said methods comprising contacting isolated or purified rat α1→2fucosyltransferase or a cellular fraction containing α1→2fucosyltransferase with GDP-fucose and a molecule having a terminal Galβ1→3GalNAc moiety. The molecule having a terminal Galβ1→3GalNAc moiety can be a glycolipid, a glycoprotein, a glycolipoprotein or a free saccharide.

Thus, the invention provides methods for the preparative synthesis of glycolipids, glycoproteins, glycolipoproteins or free oligosaccharides comprising Fucα1→2Galβ1→3GalNAc. In one embodiment, the fucosyl-glycolipid, -glycoprotein, -glycolipoprotein or -free oligosaccharide or -polysaccharide produced by the method of the invention is used as an additive to a nutritional formula.

In a particular embodiment, the invention provides a method for the preparative synthesis of fucosyl-$GM_1$ comprising contacting isolated or purified rat α1→2fucosyltransferase or a cellular fraction containing α1→2fucosyltransferase with GDP-fucose and the ganglioside $GM_1$ and recovering fucosyl-$GM_1$.

The invention provides methods for the use of fucosyl-$GM_1$ in immunotherapy for human disease comprising administering said compound to a human patient with a disease. In one embodiment, the disease is cancer or neurological disease. In a specific preferred embodiment, said patient has small cell lung carcinoma.

3.1. Abbreviations

As used herein, the following abbreviations shall have the meanings indicated.
AAF: N-2-acetylaminofluorine
α1→2FucT: α1→2fucosyltransferase
cDNA: complementary DNA
FucT, fucosyltransferase
fucosyl-$GM_1$:II$^3$NeuAcIV$^3$FucGg$_4$, Fucα1→2Galβ1→3 GalNAcβ1→4[NeuAcα2→3]Galβ1→4Glcβ1→1 Cer
ganglio-B: II$^3$NeuAcIV$^3$αGalIV$^2$FucGg$_4$, Galα1→3 [Fucα1→2]
Galβ1→3GalNAcβ1→4[NeuAcα2→3] Galβ1→4Glcβ1→1Cer
$GM_1$:II$^3$NeuAcGg$_4$, Galβ1→3GalNAcβ1→4 [NeuAcα2→3]Galβ1→4
Glcβ1→1Cer
nLc$_4$: lactoneotetraosylceramide or
Galβ1→4GcNAcβ1→3Galβ1→4Glcβ1→1Cer
PCR: polymerase chain reaction
RT-PCR: reverse transcription—polymerase chain reaction

4. BRIEF DESCRIPTION OF THE FIGURES

FIG. 1. Portions of aligned nucleotide sequences of human (SEQ ID NO.'s:12–20) and rabbit (SEQ ID NO.'s:21–29) α1→2FucT nucleic acids. The regions corresponding to forward and reverse primers used in the Example described infra in Section 6 are indicated except for Primer III (SEQ ID NO:3) which corresponds to the most 3' end of the open reading frame.

Figure 2:
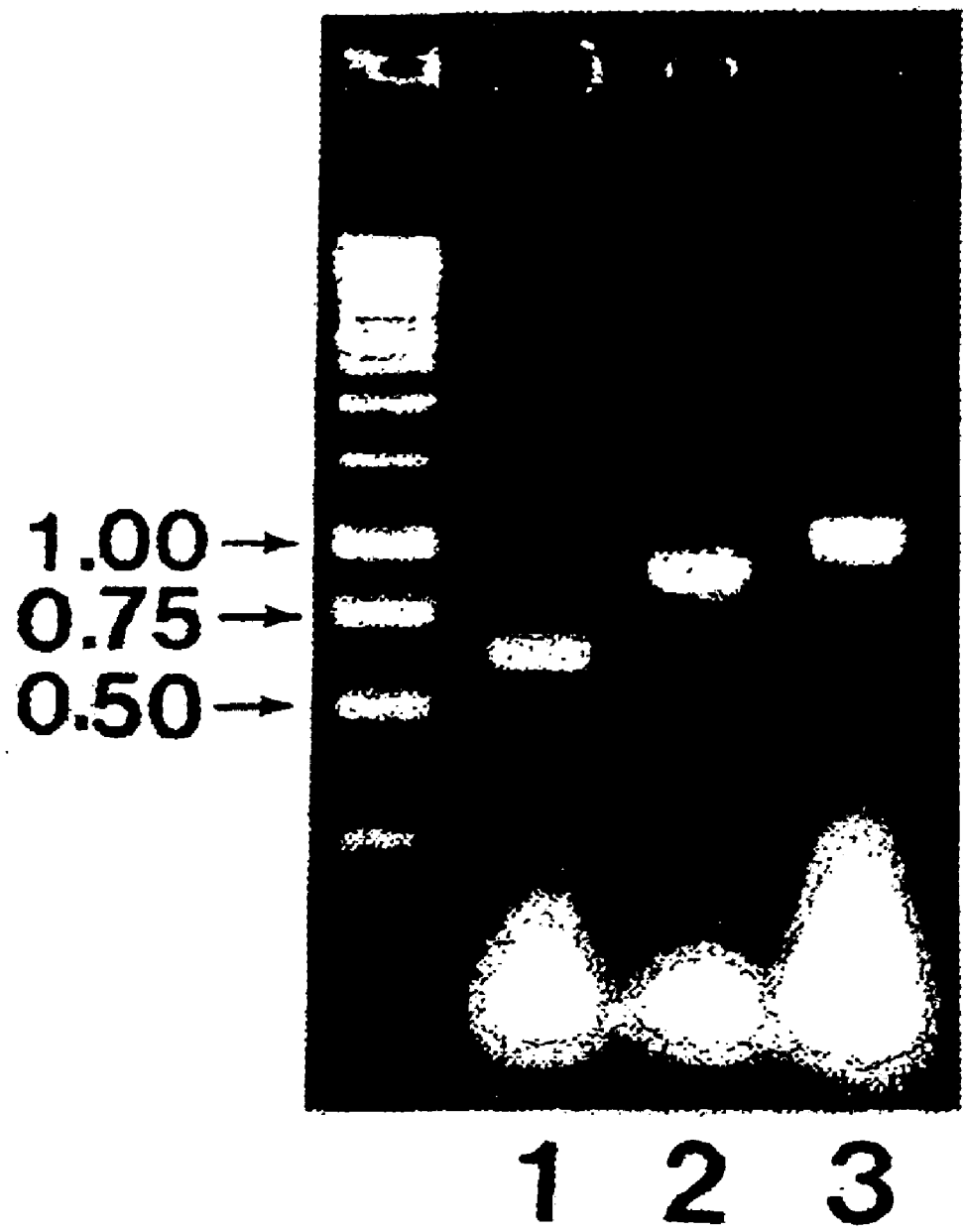

FIG. 2. RT-PCR analysis of rat hepatoma H35 cell total RNA. Lane 1, RT-PCR product generated using primers I (SEQ ID NO:1) and II (SEQ ID NO:2); lane 2, RT-PCR product generated using primers I (SEQ ID NO:1) and III (SEQ ID NO:3); lane 3, RT-PCR product generated using primers V (SEQ ID NO:5) and III (SEQ ID NO:3). Seven μl of each PCR mix was electrophoresed in a 0.8% agarose gel in 1× TBE buffer. The gel was stained with ethidium bromide. Size standards of 1.0, 0.75, and 0.5 kb are indicated.

FIGS. 3(A–B). Nucleotide (SEQ ID NO:9) and deduced amino acid sequence (SEQ ID NO:10) of the catalytic domain of rat hepatoma H35 cell α1→2FucT. FIG. 3A. Nucleotide and deduced amino acid sequence of the 1068-bp rat hepatoma H35 cell α1→2 FucT RT-PCR product generated with primers V (SEQ ID NO:5) and III (SEQ ID NO:3). The sequence extends from the second C residue following the EcoRI site in primer V through the end of primer III (SEQ ID NO:3). This nucleotide sequence has been deposited in GenBank with the Accession No. AF042743. The sequence is translated in reading frame 1. Potential N-linked glycosylation sites are shaded. The region which overlaps rat FTB is indicated by a solid line over the sequence. The amino acid differing between the H35 cell sequence and that predicted by the rat FTB sequence is underlined. The stop codon is indicated in bold lettering. FIG. 3B. Comparison of amino acid sequence homology between the catalytic domain of rat hepatoma H35 cell α1→2FucT and human Sec2 (SEQ ID NO:11).

Figure 4:
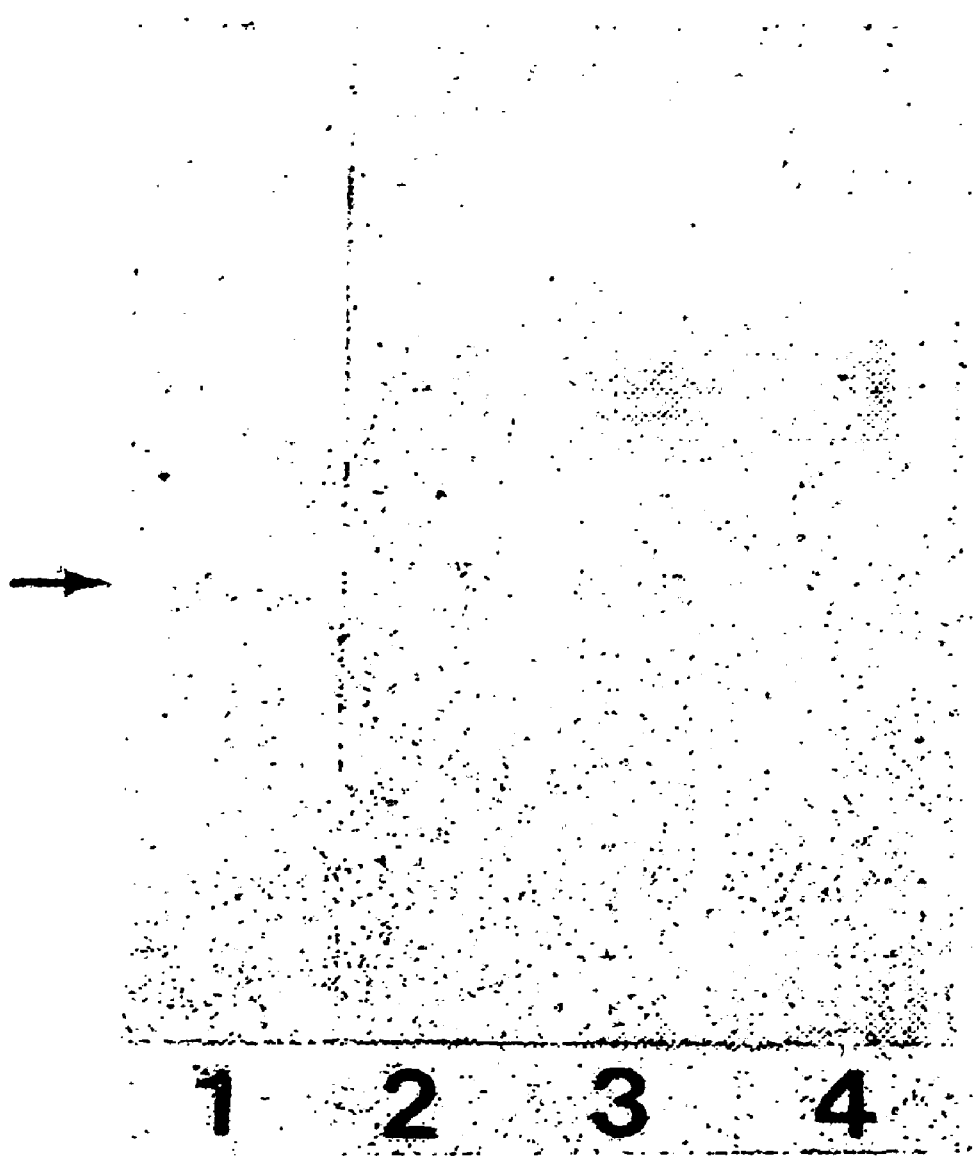

FIG. 4. TLC analysis of reaction products from transfer of [$^{14}$C]fucose to $GM_1$ and nLc$_4$ catalyzed by the pPROTA-expressed catalytic domain of rat hepatoma H35 cell α1→2FucT. Lanes 1 and 3 show results from pPROTA expressed H35 cell α1→2FucT in the forward orientation. Lanes 2 and 4 show results from pPROTA expressed H35 cell α1→2FucT in the reverse orientation. Lanes 1 and 2, transfer to $GM_1$; lanes 3 and 4,transfer to nLc$_4$. The arrow indicates the TLC mobility of standard fucosyl-$GM_1$. The solvent system was composed of $CHCl_3$:$CH_3OH$:$H_2O$ (60:40:9), containing 0.02% $CaCl_2.2H_2O$. See, infra, Section 6 for details.

FIG. 5. Nucleotide (SEQ ID NO:7) and deduced amino acid sequence (SEQ ID NO:8) of the 1140 bp rat hepatoma H35 cell α1→2FucT RT-PCR product generated with primers VI (SEQ ID NO:6) and III (SEQ ID NO:3). The entire coding region of 380 amino acids through the stop codon is represented. Potential N-linked glycosylation sites are highlighted. The region which was found to overlap rat FTB is indicated by a solid line over the sequence. The amino acid differing between the H35 sequence and that predicted by the rat FTB is underlined. The intra-cellular/transmembrane domain comprised of 81 nucleotides (27 amino acids), is shown in larger italic font.

Figure 6:
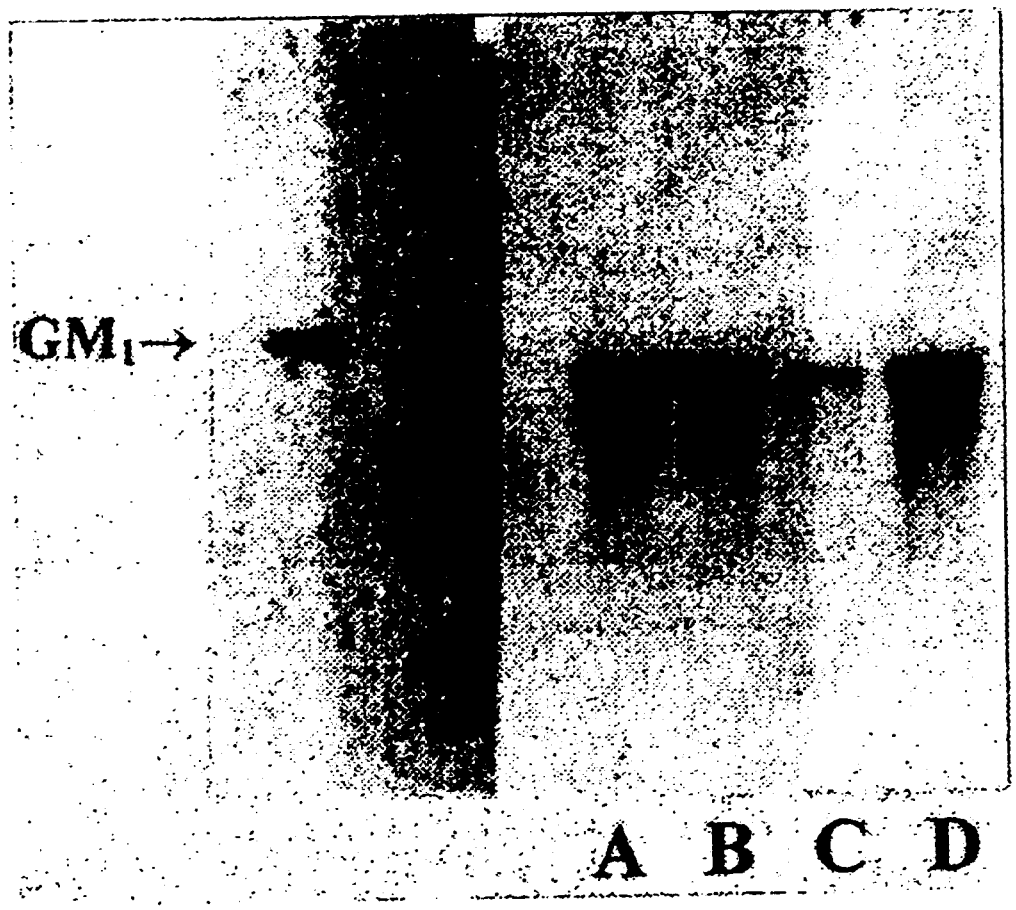

FIG. 6. TLC analysis of reaction products from transfer of [$^{14}$C] to $GM_1$ catalyzed by expressed recombinant full length rat hepatomaα1→2FucT. Lane A: transfer to $GM_1$ in absence of detergent or phospholipid; Lane B: transfer to $GM_1$ in the presence of phosphatidylglycerol (PPG), Lane C: transfer to $GM_1$ in the presence of PPG and G3634A detergent, and Lane D: transfer to $GM_1$ in the presence of CHAPSO detergent. The reactions were conducted for two hours at 37° C. $GM_1$ standard is indicated. The solvent system was composed of $CHCl_3:CH_3OH:H_2O$ (60:40:9), containing 0.02% $CaCl_2.2H_2O$. See, infra, Section 7 for details.

Figure 7:
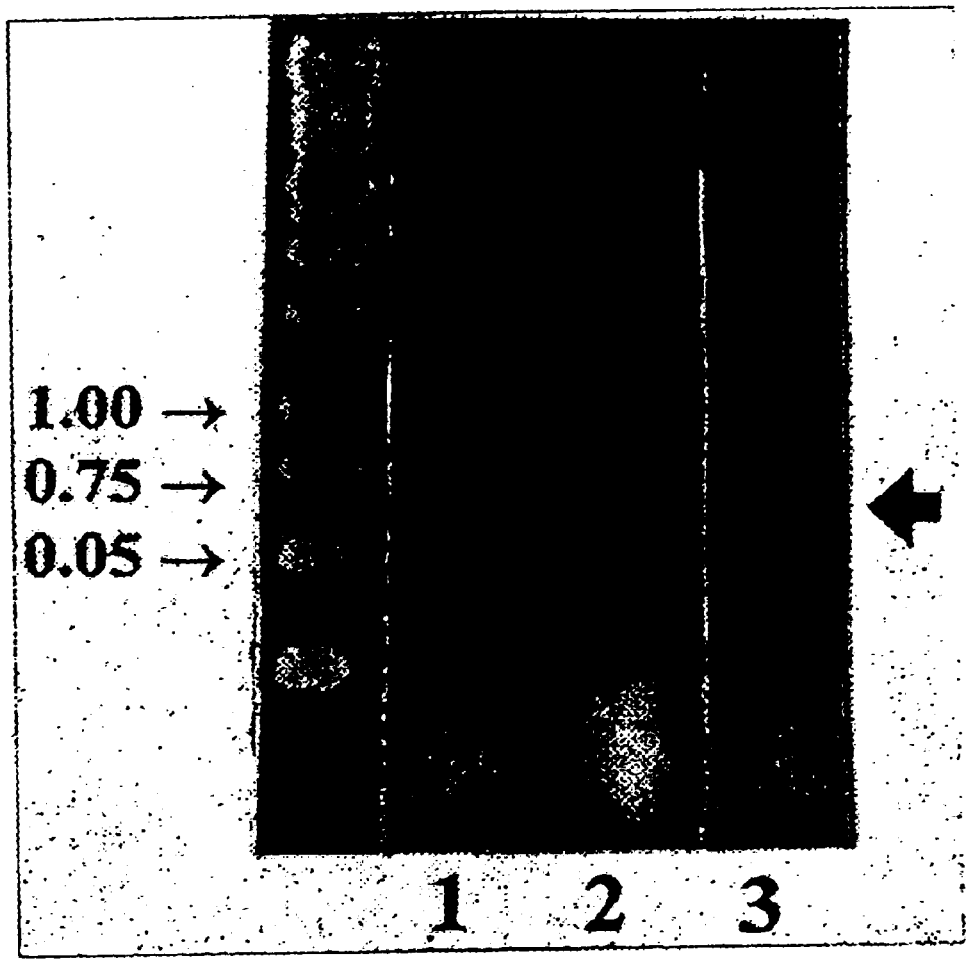

FIG. 7. PCR products generated using primers I (SEQ ID NO:1) and II (SEQ ID NO:2) in RT-PCR analysis total RNA from rat hepatoma H35 cells and from normal rat liver tissue. RT-PCR analysis was performed on Lane 1: Total RNA from rat hepatoma H35 cells, Lane 2: Total RNA from normal rat liver tissue, and Lane 3: Total RNA from AAF-fed rat liver tissue. The arrow on right indicates location of 0.6-kb PCR product. Size markers (in kb) are indicated on left. Five μl of each PCR mix was electrophoresed in a 0.8% agarose gel in 1× TBE buffer. The gel was stained with ethidium bromide. See, infra, Section 8 for details.

Figures 8A, 8B:

FIGS. 8(A–B). FIG. 8A. TLC Analysis of reaction products from transfer of [$^{14}$C] to $GM_1$ catalyzed by full length expressed recombinant α1→2FucT from COS-7 cells transfected with FL-RFT-pcDNA3 in the presence of increasing concentrations of antisense FL-RFT(-)-pcDNA3. All reactions were carried out in the presence of CHAPSO detergent. Equimolar ratios of total DNA were maintained in each transfection by including varying concentrations of pcDNA3 plasmid (vector minus insert). All lanes except Lane II were transfected with 1 μg of FL-RFT-pcDNA3. Total FL-RFT(-)-pcDNA3 transfected was as follows: Lane I—0 μg, Lane II—1.0 μg, Lane III—1.0 μg, Lane IV—2.0 μg, Lane V—3.0 μg, and Lane VI—5.0 μg. The solvent system was composed of $CHCl_3:CH_3 OH:H_2O$ (60:40:9), containing 0.02% $CaClH_2 2H_2O$. The $GM_1$ standard was visualized by spraying in 0.5% orcinol in 2 N sulfuric acid; FIG. 8B. Percentage reduction of initial α1→2FucT activity by increasing doses of FL-RFT(-)-pcDNA3. The major reaction product in each lane (indicated by arrow) (see FIG. 8A) was scraped off the plate and counted in a scintillation counter. Cpm minus background counts of 117 (Lane II) and percentage reduction of initial α1→2FucT activity by increasing doses of FL-RFT(-)-pcDNA3 are shown. See, infra, Section 9 for details.

Figure 9:
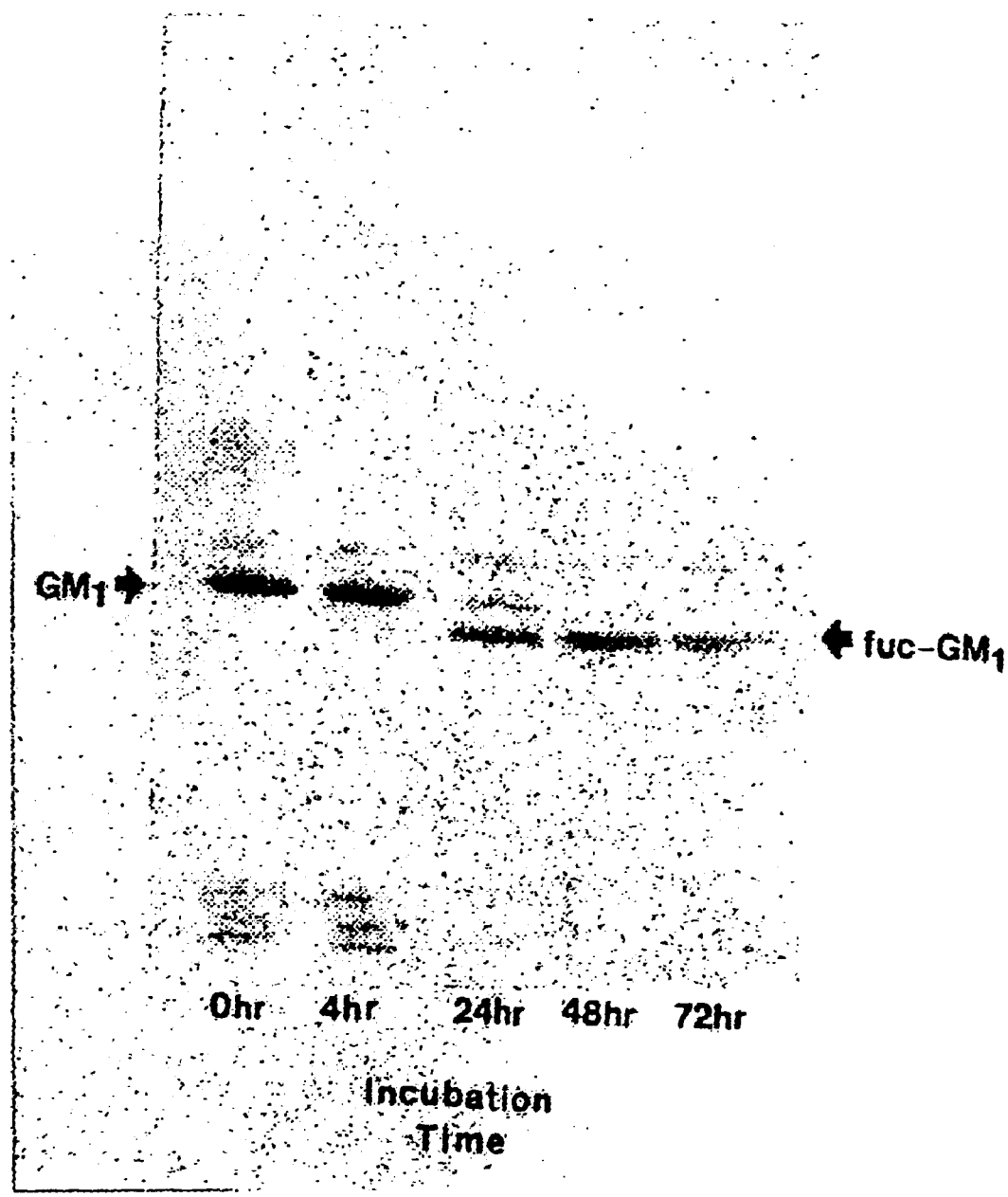

FIG. 9. Preparative in vitro biosynthesis of fucosyl-$GM_1$ utilizing recombinant rat α1→2fucosyltransferase. The results demonstrate the appearance of increasing amounts of a slower migrating band corresponding to fucosyl-$GM_1$ from transfer of fucose in the α1→2-linkage to the added $GM_1$ acceptor with time. The enzyme is very active, yielding almost complete conversion to fucosyl-$GM_1$ after 24 to 48 hours. See, infra, Section 10 for details.

5. DETAILED DESCRIPTION OF THE INVENTION

As described herein, the inventors have discovered and characterized a new ganglioside $GM_1$-specific α1→2fucosyltransferase gene, representing the first instance in which a nucleotide sequence encoding a fucosyltransferase with $GM_1$-specificity has been identified. The novel nucleotide sequence and novel encoded protein constitute very useful tools for the preparative synthesis of fucosyl-containing glycolipids, glycoproteins, glycolipoproteins and oligosaccharides. In a particular embodiment, the nucleotide sequences and encoded proteins are useful for the preparative synthesis of fucosyl-$GM_1$.

The present invention thus encompasses proteins encoded by and nucleotide sequences of a rat, $GM_1$-specific α1→2fucosyltransferase gene. The invention further encompasses derivatives and analogs of such α1→2fucosyltransferase protein. Nucleic acids encoding such derivatives or analogs are also within the scope of the invention. Production of the foregoing proteins, e.g., by recombinant methods, is provided.

The invention also encompasses α1→2fucosyltransferase protein derivatives and analogs which are functionally active, i.e., which are capable of displaying catalytic activity associated with a full-length $GM_1$-specific α1→2fucosyltransferase protein. Catalytic activity is defined as the ability to mediate the synthesis of fucosyl-$GM_1$ from starting materials consisting of the ganglioside $GM_1$ and the sugar nucleotide donor GDP-fucose.

For clarity of disclosure, and not by way of limitation, the detailed description of the invention is divided into the following subsections which describe or illustrate certain features, embodiments or applications of the invention.

5.1. Isolation of Rat α1→2Fucosyltransferase Nucleic Acids

The invention relates to the nucleotide sequences of a rat $GM_1$-specific α1→2fucosyltransferase (hereinafter α1→2FucT). The invention provides isolated or purified nucleic acids comprising an α1→2FucT encoding sequence; in another embodiment, the nucleic acids comprise the 1069 nucleotide catalytic region of an α1→2FucT sequence. Nucleic acids can be single or double stranded. The invention also relates to nucleic acids hybridizable to or complementary to the foregoing sequences or their reverse complements. In specific aspects, nucleic acids are provided which comprise a sequence complementary to at least the 1069 nucleotide catalytic of an α1→2FucT gene domain, or the entire coding region.

5.1.1. Hybridization Conditions

In a specific embodiment, a nucleic acid which is hybridizable to an α1→2FucT nucleic acid (e.g., having a sequence as set forth in SEQ ID NO:7, or to its reverse complement, or to a nucleic acid encoding an α1→2FucT derivative or analog, or to its reverse complement), under conditions of low stringency is provided. By way of example and not limitation, procedures using such conditions of low stringency are as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another specific embodiment, a nucleic acid which is hybridizable to an α1→2FucT nucleic acid, or its reverse complement, under conditions of high stringency is provided. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to an α1→2FucT nucleic acid, or its reverse complement, under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987–1997, Current Protocols, © 1994–1997 John Wiley and Sons, Inc.).

Nucleic acids encoding derivatives and analogs of α1→2FucT proteins, and α1→2FucT antisense nucleic acids are additionally provided. As is readily apparent, as used herein, a "nucleic acid encoding a fragment or portion of an α1→2FucT protein" shall be construed as referring to a nucleic acid encoding only the recited fragment or portion of the α1→2FucT protein and not the other contiguous portions of the α1→2FucT protein as a continuous sequence.

In a preferred specific embodiment, after hybridization, wash conditions are as follows. Each membrane is washed two times each for 30 minutes each at 45° C. in 40 mM sodium phosphate, pH 7,2, 5% SDS, 1 mM EDTA, 0.5% bovine serum albumin, followed by four washes each for 30 minutes in sodium phosphate, pH 7.2, 1% SDS, 1 mM EDTA, and subsequently each membrane is treated differently as described below for low, medium, or high stringency hybridization conditions. For low stringency hybridization, membranes are not washed further. For medium stringency hybridization, membranes are additionally subjected to four washes each for 30 minutes in 40 mM sodium phosphate, pH 7.2, 1% SDS, 1 mM EDTA at 55° C. For high stringency hybridization, following the washes for low stringency, membranes are additionally subjected to four washes each for 30 minutes in 40 mM sodium phosphate, pH 7.2, 1% SDS, 1 mM EDTA at 55° C., followed by four washes each for 30 minutes in sodium phosphate, pH 7.2, 1% SDS, 1 mM EDTA at 65° C.

5.1.2. Cloning Procedures

Specific embodiments for the cloning of α1→2FucT nucleic acids follow. For expression cloning (a technique well known in the art), an expression library is constructed by any method known in the art. For example, mRNA is isolated, cDNA is made and ligated into an expression vector (e.g., a bacteriophage derivative) such that it is capable of being expressed by the host cell into which it is then introduced. Various screening assays can then be used to select for the expressed α1→2FucT product. In one embodiment, anti-α1→2FucT antibodies can be used for selection.

In another embodiment, polymerase chain reaction (PCR) is used to amplify the desired sequence in a genomic or cDNA library, prior to selection. Oligonucleotide primers representing known α1→2FucT sequences can be used as primers in PCR. In a preferred aspect, the oligonucleotide primers represent at least part of conserved segments of strong homology between α1→2FucT genes of different species. Examples of useful primers are provided (the α1→2FucT coding regions and complements thereof in SEQ ID NOs:1–6). The synthetic oligonucleotides may be utilized as primers to amplify sequences from a source (RNA or DNA), preferably a cDNA library, of potential interest. PCR can be carried out, e.g., by use of a Perkin-Elmer Cetus thermal cycler and Taq polymerase (e.g., Gene Amp™). The nucleic acid being amplified can include mRNA or cDNA or genomic DNA from any species. One may synthesize degenerate primers for amplifying homologs from other species in the PCR reactions.

It is also possible to vary the stringency of hybridization conditions used in priming the PCR reactions, to allow for greater or lesser degrees of nucleotide sequence similarity between the known α1→2FucT nucleotide sequences and a nucleic acid homolog (or ortholog) being isolated. For cross species hybridization, low stringency conditions are preferred. For same species hybridization, moderately stringent conditions are preferred. After successful amplification of a segment of an α1→2FucT homolog, that segment may be cloned and sequenced by standard techniques, and utilized as a probe to isolate a complete cDNA or genomic clone. This, in turn, permits the determination of the gene's complete nucleotide sequence, the analysis of its expression, and the production of its protein product for functional analysis, as described below. In this fashion, additional nucleic acids encoding α1→2FucT proteins may be identified.

The above-described methods are not meant to limit the following general description of methods by which clones of α1→2FucT genes may be obtained.

Any eukaryotic cell potentially can serve as the nucleic acid source for molecular cloning of α1→2FucT nucleic acids. The nucleic acid sequences encoding α1→2FucT proteins may be isolated from vertebrate, mammalian, human, porcine, bovine, feline, avian, equine, canine, as well as additional primate sources, insects (e.g., Drosophila), invertebrates, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see e.g., Sambrook et al., 1989, Molecular Cloning, A Laboratory Manual, 2d Ed., Vol. I, II, Cold Spring Harbor Laboratory Press, Cold Spring Harbor, N.Y.; Glover, ed., 1985, DNA Cloning: A Practical Approach, MRL Press, Ltd., Oxford, U.K.). Clones derived from genomic DNA may contain regulatory and intron DNA regions in addition to coding regions; clones derived from cDNA will contain only exon sequences. Whatever the source, the nucleic acid should be molecularly cloned into a suitable vector for propagation of the nucleic acid sequence.

In the molecular cloning of the gene from genomic DNA, DNA fragments are generated, some of which will encode the desired gene. The DNA may be cleaved at specific sites using various restriction enzymes. Alternatively, one may use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired nucleic acid may be accomplished in a number of ways. For example, if a portion of an α1→2FucT gene or its specific RNA or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the desired nucleic acid may be detected by assays based on the physical, chemical, or immunological properties of its expressed product. For example, cDNA clones, or DNA clones which hybrid-select the proper mRNAs, can be selected and expressed to produce a protein that has, e.g., similar or identical electrophoretic migration, isoelectric focusing behavior, proteolytic digestion maps, catalytic activity, or antigenic properties as known for an α1→2FucT protein. Using an antibody to a known α1→2FucT protein, other α1→2FucT proteins may be identified by binding of the labeled antibody to expressed putative α1→2FucT proteins, e.g., in an ELISA (enzyme-linked immunosorbent assay)-type procedure. Further, using a binding protein specific to a known α1→2FucT protein, other α1→2FucT proteins may be identified by binding to such a protein (see e.g., Clemmons, 1993, Mol. Reprod. Dev. 35:368–374; Loddick et al., 1998, Proc. Natl. Acad. Sci. U.S.A. 95:1894–1898).

An α1→2FucT nucleic acid can also be identified by mRNA selection using nucleic acid hybridization followed by in vitro translation. In this procedure, fragments are used to isolate complementary mRNAs by hybridization. Such DNA fragments may represent available, purified α1→2FucT DNA of another species (e.g., mouse, human). Immunoprecipitation analysis or functional assays (e.g., catalytic activity, etc.) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against α1→2FucT protein. A radiolabeled α1→2FucT cDNA can be synthesized using the selected mRNA (from the adsorbed polysomes) as a template. The radiolabeled mRNA or cDNA may then be used as a probe to identify the α1→2FucT DNA fragments from among other genomic DNA fragments.

Alternatives to isolating the α1→2FucT genomic DNA include, but are not limited to, chemically synthesizing the nucleic acid sequence itself from a known sequence or making cDNA to the mRNA which encodes the α1→2FucT protein. For example, RNA for cDNA cloning of the α1→2FucT gene can be isolated from cells which express the gene.

The identified and isolated nucleic acid can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene USA, La Jolla, Calif.). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and an α1→2FucT nucleic acid may be modified by homopolymeric tailing. Recombinant molecules can be introduced into host cells via transformation, transfection, infection, electroporation, etc., so that many copies of the nucleic acid sequence are generated.

In an alternative method, the desired nucleic acid may be identified and isolated after insertion into a suitable cloning vector in a "shot gun" approach. Enrichment for the desired nucleic acid, for example, by size fractionization, can be done before insertion into the cloning vector.

In an additional embodiment, the desired nucleic acid may be identified and isolated after insertion into a suitable cloning vector using a strategy that combines a "shot gun" approach with a "directed sequencing" approach. Here, for example, the entire DNA sequence of a specific region of the genome, such as a sequence tagged site (STS), can be obtained using clones that molecularly map in and around the region of interest.

In specific embodiments, transformation of host cells with recombinant DNA molecules that incorporate an isolated α1→2FucT gene, cDNA, or synthesized DNA sequence enables generation of multiple copies of the gene. Thus, the nucleic acid may be obtained in large quantities by growing transformants, isolating the recombinant DNA molecules from the transformants and, when necessary, retrieving the inserted nucleic acid from the isolated recombinant DNA.

The α1→2FucT sequences provided by the instant invention include those nucleotide sequences encoding substantially the same amino acid sequences as found in native α1→2FucT proteins, and those encoded amino acid sequences with functionally equivalent amino acids, as well as those encoding other α1→2FucT derivatives or analogs, as described in below for α1→2FucT derivatives and analogs.

5.2. Expression of a Rat α1→2Fucosyltransferase Coding Sequence

The nucleotide sequence coding for an α1→2FucT protein or a functionally active analog or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native α1→2FucT gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In yet another embodiment, a fragment of an α1→2FucT protein comprising one or more domains of the α1→2FucT protein is expressed.

Any of the methods previously described for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of a nucleic acid sequence encoding an α1→2FucT protein or peptide fragment may be regulated by a second nucleic acid sequence so that the α1→2FucT protein or peptide is expressed in a host transformed with the recombinant DNA molecule. For example, expression of an α1→2FucT protein may be controlled by any promoter/enhancer element known in the art. A promoter/enhancer may be homologous (i.e. native) or herterologous (i.e. not native). Promoters which may be used to control the expression of α1→2FucT coding sequences include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), prokaryotic expression vectors such as the β-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25; Scientific American, 1980, 242:74–94), plant expression vectors comprising the nopaline synthetase promoter region (Herrera-Estrella et al., Nature 303:209–213), the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120), promoter elements from yeast or other fungi such as the Gal4-responsive promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to an α1→2FucT nucleic acid, one or more origins of replication, and, optionally, one or more selectable markers (e.g., an antibiotic resistance gene).

In a specific embodiment, the promoter that is operably linked to the rat α1→2FucT nucleic acid is not the native rat α1→2FucT gene promoter (i.e. it is a heterologous promoter).

In a specific embodiment, an expression construct is made by subcloning an α1→2FucT coding sequence into the EcoRI restriction site of the pPROTA mammalian cell expression vector (Henion et al., 1994, Glycobiology 4:193–202). This allows for the expression of the α1→2FucT protein product from the subclone fused to the IgG binding domain of protein A.

In another specific embodiment, an expression construct is made by subcloning an α1→2FucT coding sequence into the pcDNA3 expression vector (Invitrogen Corp., Carlsbad, Calif.). This allows for high level expression of the α1→2FucT protein product from the subclone.

In another specific embodiment, an expression construct is made by subcloning an α1→2FucT coding sequence into the pichia pPIC9 expression vector (Invitrogen Corp., Carlsbad, Calif.). This allows for high level expression of the α1→2FucT protein product from the subclone.

Expression vectors containing α1→2FucT coding sequence inserts can be identified by four general approaches: (a) nucleic acid hybridization; (b) molecular biology, (c) expression of inserted sequences; and (d) presence or absence of "marker" gene functions. In the first approach, the presence of an α1→2FucT nucleic acid inserted in an expression vector can be detected by nucleic acid hybridization using probes comprising sequences that are homologous to an inserted α1→2FucT nucleic acid. In the second approach, a combination of molecular biology and "marker" gene function are used to identify recombinant expression vectors containing the α1→2FucT insert. For example, if the α1→2FucT nucleic acid is inserted in the EcoRI site of the pcDNA3 vector, which codes for both Ampicillin and Neomycin resistance, bacterial cells that take up the vector are identified by their resistance to Ampicillin and/or Neomycin, and those vectors containing the α1→2FucT insert can be identified by restriction digestion of the amplified vector DNA with EcoRI. In the third approach, recombinant expression vectors can be identified by assaying the α1→2FucT product expressed by the recombinant. Such assays can be based, for example, on the physical or functional properties of the α1→2FucT protein in in vitro assay systems, e.g., the catalysis of fucosyl-GM$_1$ synthesis. In the fourth approach, the vector/host system can be identified based upon the presence or absence of certain "marker" gene functions (e.g., thymidine kinase activity, β-galactosidase, resistance to antibiotics, transformation phenotype, occlusion body formation in baculovirus, etc.) caused by the insertion of an α1→2FucT nucleic acid in the vector. For example, if the α1→2FucT nucleic acid is inserted within the marker gene sequence of the vector, recombinants containing the α1→2FucT insert can be identified by the absence of the marker gene function.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda phage), and plasmid and cosmid DNA vectors, to name but a few.

In addition, a host cell strain may be chosen which modulates the expression of the inserted sequences, or modifies and processes the nucleic acid product in the specific fashion desired. Expression from certain promoters can be elevated in the presence of certain inducers; thus, expression of the genetically engineered α1→2FucT protein may be controlled. Furthermore, different host cells have characteristic and specific mechanisms for the translational and post-translational processing and modification (e.g., glycosylation) of proteins. Appropriate cell lines or host systems can be chosen to ensure the desired modification and processing of the foreign protein expressed. For example, expression in a bacterial system can be used to produce a soluble α1→2FucT catalytic domain. Expression in animal cells can be used to ensure folding, proper membrane insertion and glycosylation of α1→2FucT.

In other specific embodiments, the α1→2FucT protein, derivative or analog may be expressed as a fusion, or chimeric protein product (comprising the protein, derivative or analog joined via a covalent bond such a peptide bond to a heterologous protein sequence (of a different protein)). A chimeric protein may include fusion of the α1→2FucT protein, derivative or analog to a second protein or at least a portion thereof, wherein a portion is one (preferably 10, 15, or 20) or more amino acids of said second protein. The second protein, or one or more amino acid portion thereof, may be from a different rat α1→2FucT protein or may be from a protein that is not a rat α1→2FucT protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, the amino acid portion of the second protein is one that allows for the extracellular secretion of the α1→2FucT catalytic domain, e.g. the Ig binding domain of protein A (Henion et al., 1994, Glycobiology 4:193–202). In a specific embodiment, the amino acid portion of the second protein is one that allows for the membrane localization of the α1→2FucT catalytic domain, e.g. the type I transmembrane domain of sevenless (Basler et al., 1991) or Notch (reviewed by Weinmaster, 1997, Mol. Cell. Neurosci. 9:91–102), the type II transmembrane domain of human H-type α1→2fucosyltransferase (Koda et al., 1997, Eur. J. Biochem. 300:623–626), or the myristylation signal of src proteins (Cross et al., 1984, Mol. Cell Biol. 4:1834–1842; Simon et al., 1985, Cell 42:831–840).

5.3. Identification and Purification of Rat α1→2FucT Products

In particular aspects, the invention provides amino acid sequences of α1→2FucT proteins and derivatives or analogs thereof which comprise an antigenic determinant (i.e., can be recognized by an antibody) or which are otherwise functionally active, as well as nucleic acid sequences encoding the foregoing. "Functionally active" α1→2FucT material as used herein refers to that material displaying one or more functional activities associated with a full-length (wild-type) α1→2FucT protein, e.g., enzymatic ability to transfer fucose or a fucosyl moiety in an α1→2 linkage to a terminal galactose of a Galβ1→3GalNAc moiety, e.g. $GM_1$, with specificity, etc.

Once a recombinant nucleic acid which expresses the α1→2FucT coding sequence is identified, the product can be analyzed. This is achieved by assays based on the physical or functional properties of the product, including radioactive labeling of the product followed by analysis by gel electrophoresis, immunoassay, etc.

Once the α1→2FucT protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see, e.g., Section 5.7).

Alternatively, once an α1→2FucT protein produced by a recombinant is identified, the amino acid sequence of the protein can be deduced from the nucleotide sequence of the chimeric nucleic acid. As a result, the protein can be synthesized by standard chemical methods known in the art (e.g., see Hunkapiller et al., 1984, Nature 310:105–111).

In another alternate embodiment, native α1→2FucT proteins can be purified from natural sources, by standard methods such as those described above (e.g., immunoaffinity purification).

In a specific embodiment of the present invention, such α1→2FucT proteins, whether produced by recombinant DNA techniques or by chemical synthetic methods or by purification of native proteins, include but are not limited to those containing, as a primary amino acid sequence, all or part of the amino acid sequence substantially as depicted in FIG. 5 (SEQ ID NO:8), as well as derivatives and analogs thereof, including proteins homologous thereto.

5.4. Structure of α1→2FucT Nucleic Acids and Proteins

The structure of α1→2FucT nucleic acids and proteins of the invention can be analyzed by various methods known in the art. Some examples of such methods are described below.

5.4.1. Genetic Analysis

The cloned DNA or cDNA corresponding to an α1→2FucT nucleic acid can be analyzed by methods including but not limited to Southern hybridization (Southern, 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, 1982, Molecular Cloning, A Laboratory Manual, Cold Spring Harbor Laboratory Press, Cold Spring Harbor, N.Y.), and DNA sequence analysis. Accordingly, this invention provides nucleic acid probes recognizing an α1→2FucT nucleic acid. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with an α1→2FucT-specific probe can allow the detection of an α1→2FucT gene in DNA from various cell types. Methods of amplification other than PCR are commonly known and can also be employed. In one embodiment, Southern hybridization can be used to determine the genetic linkage of an α1→2FucT gene. Northern hybridization analysis can be used to determine the expression of an α1→2FucT gene. Various cell types, at various states of development or activity can be tested for α1→2FucT gene expression. The stringency of the hybridization conditions for both Southern and Northern hybridization can be manipulated to ensure detection of nucleic acids with the desired degree of relatedness to the specific α1→2FucT-probe used. Modifications of these methods and other methods commonly known in the art can be used.

Restriction endonuclease mapping can be used to roughly determine the genetic structure of an α1→2FucT nucleic acid. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. Protein Analysis

The amino acid sequence of an α1→2FucT protein can be derived by deduction from the DNA sequence, or alternatively, by direct sequencing of the protein, e.g., with an automated amino acid sequencer.

An α1→2FucT protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of the α1→2FucT protein and the corresponding regions of the gene sequence which encode such regions.

Structural prediction analysis (Chou and Fasman, 1974, Biochemistry 13:222) can also be done, to identify regions of an α1→2FucT protein that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, 1974, Biochem. Exp. Biol. 11:7–13), nuclear magnetic resonance spectroscopy (Clore and Gonenborn, 1989, CRC Crit. Rev. Biochem. 24:479–564) and computer modeling (Fletterick and Zoller, 1986, Computer Graphics and Molecular Modeling, in *Current Communications in Molecular Biology,* Cold Spring Harbor Laboratory Press, Cold Spring Harbor, N.Y.).

5.5. Antibodies

According to the invention, α1→2FucT protein, its derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In another embodiment, antibodies to a domain (e.g., an α1→2FucT receptor binding domain) of an α1→2FucT protein are produced. In aspecific embodiment, fragments of an α1→2FucT protein identified as hydrophilic are used as immunogens for antibody production.

Various procedures known in the art may be used for the production of polyclonal antibodies to an α1→2FucT protein or derivative or analog. In a particular embodiment, rabbit polyclonal antibodies to an epitope of an α1→2FucT protein consisting of the sequence of SEQ ID NO:2, or a subsequence thereof, can be obtained. For the production of antibody, various host animals can be immunized by injection with the native α1→2FucT protein, or a synthetic version, or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed to an α1→2FucT protein sequence or analog thereof, any technique which provides for the production of antibody molecules by continuous cell lines in culture may be used. For example, the hybridoma technique originally developed by Kohler and Milstein, (Kohler and Milstein 1975, Nature 256:495–497), as well as the trioma technique, the human B-cell hybridoma technique (Kozbor et at., 1983, Immunology Today 4:72), and the EBV-hybridoma technique to produce human monoclonal antibodies (Cole et al., 1985, in *Monoclonal Antibodies and Cancer Therapy,* Alan R. Liss, Inc., pp. 77–96). In an additional embodiment of the invention, monoclonal antibodies can be produced in germfree animals utilizing recent technology (see e.g., PCT/US90/02545). According to the invention, human antibodies may be used and can be obtained by using human hybridomas (Cole et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for an α1→2FucT protein together with genes from a human antibody molecule of appropriate biological activity can be used; such antibodies are within the scope of this invention.

According to the invention, techniques described for the production of single chain antibodies (U.S. Pat. No. 4,946,778) can be adapted to produce α1→2FucT-specific single chain antibodies. An additional embodiment of the invention utilizes the techniques described for the construction of Fab' expression libraries (Huse et al., 1989, Science 246:1275–1281) to allow rapid and easy identification of monoclonal Fab fragments with the desired specificity for α1→2FucT proteins, derivatives, or analogs.

Antibody fragments which contain the idiotype of the molecule can be generated by known techniques. For example, such fragments include but are not limited to, the $F(ab')_2$ fragment which can be produced by pepsin digestion of the antibody molecule, the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art (e.g., enzyme-linked immunosorbent assay or ELISA). For example, to select antibodies which recognize a specific domain of a α1→2FucT protein, one may assay generated hybridomas for a product which binds to a α1→2FucT fragment containing such domain. For selection of an antibody that specifically binds a first α1→2FucT homolog but which does not specifically bind a different α1→2FucT homolog, one can select on the basis of positive binding to the first α1→2FucT homolog and a lack of binding to the second α1→2FucT homolog.

Antibodies specific to a domain of an α1→2FucT protein are also provided. Antibodies specific to an epitope of an α1→2FucT protein are also provided.

The foregoing antibodies can be used in methods known in the art relating to the localization and activity of the α1→2FucT protein sequences of the invention, erg., for imaging these proteins, measuring levels thereof in appropriate physiological samples, in diagnostic methods, etc.

5.6. α1→2FucT Proteins and Derivatives

The invention further encompasses α1→2FucT proteins, derivatives, analogs, and molecules of α1→2FucT proteins. As used herein, a molecule defined by a particular SEQ ID NO, shall be construed to mean that the sequence of that molecule comprises that SEQ ID NO, unless explicitly indicated otherwise to mean that the sequence of the molecule consists of that SEQ ID NO. Nucleic acids encoding α1→2FucT protein derivatives and protein analogs are also provided. In one embodiment, the α1→2FucT proteins are encoded by the α1→2FucT nucleic acids described in Section 5.1 above. In particular aspects, the proteins, derivatives, or analogs are of α1→2FucT proteins encoded by the amino acid sequence of (SEQ ID NO:8).

The production and use of derivatives and analogs related to an α1→2FucT protein are within the scope of the present invention. In a specific embodiment, the derivative or analog is functionally active, i.e., capable of exhibiting one or more functional activities associated with a full-length, wild-type α1→2FucT protein. As one example, such derivatives or analogs which have the desired immunogenicity or antigenicity can be used in immunoassays, for immunization, for inhibition of α1→2FucT activity, etc. As another example, such derivatives or analogs which have the desired binding activity can be used for binding to the InR gene product. As yet another example, such derivatives or analogs which have the desired binding activity can be used for binding to a binding protein specific for a known α1→2FucT protein (see e.g., Clemmons, 1993, Mol. Reprod. Dev. 35:368–374; Loddick et al., 1998, Proc. Natl. Acad. Sci. U.S.A. 95:1894–1898). Derivatives or analogs that retain, or alternatively lack or inhibit, a desired α1→2FucT protein property-of-interest (e.g., binding to an α1→2FucT protein binding partner), can be used as inducers, or inhibitors, respectively, of such property and its physiological correlates. A specific embodiment relates to an α1→2FucT protein fragment that can be bound by an anti-α1→2FucT protein antibody. Derivatives or analogs of an α1→2FucT protein can be tested for the desired activity by procedures known in the art, including but not limited to the assays described in Section (5.10 and 5.11 below).

In particular, α1→2FucT derivatives can be made by altering α1→2FucT sequences by substitutions, additions (e.g., insertions) or deletions that provide for functionally equivalent molecules. Due to the degeneracy of nucleotide coding sequences, other DNA sequences which encode substantially the same amino acid sequence as an α1→2FucT nucleic acid may be used in the practice of the present invention. These include but are not limited to nucleotide sequences comprising all or portions of an α1→2FucT nucleic acid which is altered by the substitution of different codons that encode a functionally equivalent amino acid residue within the sequence, thus producing a silent change. Likewise, the α1→2FucT derivatives of the invention include, but are not limited to, those containing, as a primary amino acid sequence, all or part of the amino acid sequence of an α1→2FucT protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins consisting of or comprising a fragment of an α1→2FucT protein consisting of at least 10 (continuous) amino acids of the α1→2FucT protein are provided. In other embodiments, the fragment consists of at least 20 or at least 50 amino acids of the α1→2FucT protein. In specific embodiments, such fragments are not larger than 35, 100 or 200 amino acids. Derivatives or analogs of α1→2FucT proteins include but are not limited to those molecules comprising regions that are substantially homologous to an α1→2FucT protein or fragment thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding α1→2FucT gene sequence, under high stringency, moderate stringency, or low stringency conditions.

Specifically, by way of example computer programs for determining homology may include but are not limited to TBLASTN, BLASTP, FASTA, TFASTA, and CLUSTALW (Altschul et al., 1990, J. Mol. Biol. 215(3):403–10; see, Pearson and Lipman, 1988, Proc. Natl. Acad. Sci. USA 85(8):2444–8; Thompson, et al., 1994, Nucleic Acids Res. 22(22):4673–80; Higgins, et al., 1996, Methods Enzymol 266:383–402).

Basic Local Alignment Search Tool (BLAST) (Altschul et al., 1990, J. of Molec. Biol., 215:403–410. "The BLAST Algorithm"; Altschul et al., 1997, Nuc. Acids Res. 25:3389–3402) is a heuristic search algorithm tailored to searching for sequence similarity which ascribes significance using the statistical methods of Karlin and Altschul 1990, Proc. Nat'l Acad. Sci. USA, 87:2264–68; 1993, Proc. Nat'l Acad. Sci. USA 90:5873–77. Five specific BLAST programs perform the following tasks: 1) The BLASTP program compares an amino acid query sequence against a protein sequence database; 2) The BLASTN program compares a nucleotide query sequence against a nucleotide sequence database; 3) The BLASTX program compares the six-frame conceptual translation products of a nucleotide query sequence (both strands) against a protein sequence database; 4) The TBLASTN program compares a protein query sequence against a nucleotide sequence database translated in all six reading frames (both strands); 5) The TBLASTX program compares the six-frame translations of a nucleotide query sequence against the six-frame translations of a nucleotide sequence database.

Smith-Waterman (database: European Bioinformatics Institute (Smith-Waterman, 1981, J. of Molec. Biol., 147:195–197) is a mathematically rigorous algorithm for sequence alignments.

FASTA (see Pearson et al., 1988, Proc. Nat'l Acad. Sci. USA, 85:2444–2448) is a heuristic approximation to the Smith-Waterman algorithm.

For a general discussion of the procedure and benefits of the BLAST, Smith-Waterman and FASTA algorithms see Nicholas et al., 1998, "A Tutorial on Searching Sequence Databases and Sequence Scoring Methods" and references cited therein.

The α1→2FucT derivatives and analogs of the invention can be produced by various methods known in the art. The manipulations which result in their production can occur at the gene or protein level. For example, a cloned α1→2FucT nucleic acid sequence can be modified by any of numerous strategies known in the art (Sambrook et al., 1989, *Molecular Cloning, A Laboratory Manual*, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified nucleic acid encoding a derivative or analog of an α1→2FucT protein, care should be taken to ensure that the modified nucleic acid remains within the same translational reading frame as the native protein, uninterrupted by translational stop signals, in the gene region where the desired α1→2FucT protein activity is encoded.

Additionally, an α1→2FucT nucleic acid sequence can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), PCR with primers containing a mutation, etc.

Manipulations of an α1→2FucT protein sequence may also be made at the protein level. Included within the scope of the invention are α1→2FucT protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In addition, analogs and derivatives of an aα1→2FucT protein can be chemically synthesized. For example, a peptide corresponding to a portion of an α1→2FucT protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the α1→2FucT sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, an α1→2FucT protein derivative is a chimeric or fusion protein comprising an α1→2FucT protein or fragment thereof (preferably consisting of at least a domain or motif of the α1→2FucT protein, or at least 10 amino acids of the α1→2FucT protein) joined at its amino- or carboxy-terminus via a peptide bond to an amino acid sequence of a different protein. In specific embodiments, the amino acid sequence of the different protein is at least 6, 10, 20 or 30 continuous amino acids of the different proteins or a portion of the different protein that is functionally active. In one embodiment, such a chimeric protein is produced by recombinant expression of a nucleic acid encoding the protein (comprising an α1→2FucT-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising the whole α1→2FucT open reading frame or the nucleotides encoding the catalytic domain fused to any heterologous protein-encoding sequences may be constructed.

In another specific embodiment, the α1→2FucT derivative is a molecule comprising a region of homology with the full length or catalytic domain of α1→2FucT protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to an α1→2FucT catalytic domain (see Section 5.6.1) or a portion thereof.

5.7. Elimination of α1→2FucT Activity

The present invention provides for methods of creating cells lacking α1→2fucosyltransferase activity.

In one embodiment, loss-of-function phenotypes are generated by antisense RNA methods (Schubiger and Edgar, 1994, Methods in Cell Biology 44:697–713). One form of the antisense RNA method involves the injection of cells with an antisense RNA that is partially homologous to the gene-of-interest (in this case an α1→2FucT nucleic acid). Another form of the antisense RNA method involves expression of an antisense RNA partially homologous to the gene-of-interest by operably joining a portion of the gene-of-interest in the antisense orientation to a powerful promoter that can drive the expression of large quantities of antisense RNA, either generally throughout the animal or in specific tissues.

In a second embodiment, loss-of-function phenotypes are generated by cosuppression methods (Bingham, 1997, Cell 90(3):385–7; Smyth, 1997, Curr. Biol. 7(12):793–5; Que and Jorgensen, 1998, Dev. Genet. 22(1):100–9). Cosuppression is a phenomenon of reduced gene expression produced by expression or injection of a sense strand RNA corresponding to a partial segment of the gene-of-interest. Cosuppression effects have been employed extensively in plants to generate loss-of-function phenotypes.

5.7.1. Antisense Regulation of Gene Expression

The invention provides for antisense uses of rat α1→2FucT nucleic acids. In a specific embodiment, an α1→2FucT protein function is inhibited by use of α1→2FucT antisense nucleic acids. The present invention provides for use of nucleic acids of at least six nucleotides that are antisense to a gene or cDNA encoding an α1→2FucT protein or a portion thereof. An α1→2FucT "antisense" nucleic acid as used herein refers to a nucleic acid capable of hybridizing to a sequence-specific (i.e. non-poly A) portion of an α1→2FucT RNA (preferably mRNA) by virtue of some sequence complementarity. Antisense nucleic acids may also be referred to as inverse complement nucleic acids. The antisense nucleic acid may be complementary to a coding and/or noncoding region of an α1→2FucT mRNA. Such antisense nucleic acids have utility in inhibiting an α1→2FucT protein function.

The antisense nucleic acids of the invention can be oligonucleotides that are double-stranded or single-stranded, RNA or DNA or a modification or derivative thereof, which can be directly administered to a cell. The α1→2FucT antisense nucleic acids of the invention are preferably oligonucleotides (ranging from 6 to about 50 oligonucleotides). In specific aspects, an oligonucleotide is at least 10 nucleotides, at least 15 nucleotides, at least 100 nucleotides, or at least 200 nucleotides in length. The oligonucleotide can be DNA or RNA or chimeric mixtures or derivatives or modified versions thereof, or single-stranded or double-stranded. The oligonucleotide can be modified at the base moiety, sugar moiety, or phosphate backbone. The oligonucleotide may include other appending groups such as peptides, or agents facilitating transport across the cell membrane (see e.g., Letsinger et al., 1989, Proc. Natl. Acad. Sci. U.S.A. 86:6553–6556; Lemaitre et al., 1987, Proc. Natl. Acad. Sci. U.S.A. 84:648–652; PCT Publication No. WO 88/09810, published Dec. 15, 1988) or the blood-brain barrier (see e.g., PCT Publication No. WO 89/10134, published Apr. 25, 1988), hybridization-triggered cleavage agents (see e.g., Krol et al., 1988, BioTechniques 6:958–976) or intercalating agents (see e.g., Zon, 1988, Pharm. Res. 5:539–549).

In a preferred aspect of the invention, an α1→2FucT antisense oligonucleotide is provided as single-stranded DNA. In another preferred aspect, such an oligonucleotide comprises a sequence antisense to the sequence encoding a B peptide domain or an A peptide domain of an α1→2FucT protein. The oligonucleotide may be modified at any position on its structure with substituents generally known in the art.

The α1→2FucT antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide may be conjugated to another molecule, e.g., a peptide, a hybridization-triggered cross-linking agent, a transport agent, a hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (Stein et al., 1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, an α1→2FucT antisense oligonucleotide comprises catalytic RNA, or a ribozyme (see e.g., PCT Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In a preferred embodiment, the antisense nucleic acids of the invention are expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the α1→2FucT antisense nucleic acid. Such a vector can remain episomal or become chromosomally integrated, as long as it can be transcribed to produce the desired antisense RNA. The antisense nucleic acid can be administered by use of an adenoviral or retroviral vector (see U.S. Pat. No. 4,980,286), by direct injection, or by use of microparticle bombardment (e.g., a gene gun; Biolistic, Dupont), by coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Vectors can be constructed by recombinant DNA technology methods standard in the art. Vectors can be plasmid, viral, or others known in the art, used for replication and expression in mammalian cells. Expression of the sequence encoding the α1→2FucT antisense RNA can be by any promoter known in the art. Such promoters can be inducible or constitutive. Such promoters include but are not limited to: the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a sequence-specific portion of an RNA transcript of an α1→2FucT gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded α1→2FucT antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an α1→2FucT RNA it may contain and still form a stable duplex (or triplex, as the case may be). One skilled in the art can ascertain a tolerable degree of mismatch by use of standard procedures to determine, e.g., the melting point of the hybridized complex.

5.8. Biochemical Assays Using α1→2FucT Proteins

The functional activity of α1→2FucT proteins or derivatives can be assayed by various methods known to one skilled in the art.

For example, as illustrated in Section 6.3.2, infra, the activity of α1→2fucosyltransferase coupled to the IgG-binding domain of Protein A can be determined in reaction mixtures containing 2.5 μmol of HEPES buffer, pH7.2, 30 μg of $GM_1$. ganglioside or $nLc_4$, 250 μg phosphatidylglycerol, 1 μmol of $MnCl_2$, 0.5 μmol of CDP-choline, 15 nmol of GDP-[$^{14}$C]fucose (15,000 cpm/nmol), and bound to IgG-agarose beads in a total volume of 0.1 ml. The reaction mixtures are incubated for 2 h at 37° C., terminated by the addition of 0.1 ml of $CHCl_3$:$CH_3OH$ (2:1), streaked onto 4-cm-wide strips of Whatman 3 paper and developed with water overnight. The papers are dried and the labeled product extracted from the origins with 2- to 5-ml washes of $CHCl_3$:$CH_3OH$:$H_2O$ (10:5:1). The combined eluates are concentrated to dryness by an $N_2$ stream and dissolved in 20 μl of $CHCl_3$:$CH_3OH$ (2:1). A 10-μl aliquot of each is spotted onto a HP-TLC plate (Merck)and developed in a solvent system composed of $CHCl_3$:$CH_3OH$:$H_2O$ (60:40:9), 0.02% $CaCl_2.2H_2O$. The radioactive products were located by autoradiography.

5.9. Additional Applications and Uses of α1→2FucT Nucleic Acids and Proteins

Provided below are additional non-limiting methods of using the α1→2FucT nucleic acids and proteins of the invention.

5.9.1. Detection of Oncogenesis

As α1→2FucT expression is often activated during oncogenic transformation (see Section 2.5 supra), oncogenic transformation of test tissues can be detected by assaying for changes in the expression of α1→2FucT, for example by the methods described below.

Assays for changes in gene expression are well known in the art (see e.g., PCT Publication No. WO 96/34099, published Oct. 31, 1996, which is incorporated by reference herein in its entirety).

In particular, the assays may detect the presence of increased or decreased expression of α1→2FucT gene or protein on the basis of increased or decreased mRNA expression (using, e.g., nucleic acid probes), increased or decreased levels of related protein products (using, e.g., the antibodies disclosed herein), or increased or decreased levels of expression of the catalytic product of the α1→2FucT gene (e.g. Fucosyl-$GM_1$).

5.9.2. Gene Therapy

As α1→2FucT expression is often activated in cell transformation, e.g. small cell lung carcinoma, down-regulation of α1→2FucT expression, e.g. by anti-sense nucleic acids to α1→2FucT coding sequences, may be used to inhibit, suppress or treat cancer(see, supra, Section 5.7). In one illustrative example, the anti-sense sequences are transduced in viral vectors, e.g. adenoviral or retroviral vectors.

5.9.3. Preparative Synthesis of Fucosyl-Saccharide Compositions

The specificity of α1→2FucT of the invention lies in its recognition of the carbohydrate structure, Galβ1→3GalNAc, when found at the terminus of a molecule. While the enzyme is utilized in vivo to catalyze the addition of fucose in an α1→2 linkage to the terminal galactose residue of the ganglioside $GM_1$, in vitro it is used to catalyze the addition of fucose in an α1→2 linkage to the terminal galactose residue of any molecule having a terminal Galβ1→3GalNAc moiety. Such molecules include glycoproteins, glycolipids, glycolipoproteins and oligo- or poly-saccharides.

The α1→2FucT proteins of the invention may be used in any of numerous forms known in the art, e.g., as an isolated or purified protein in solution, in a cellular fraction of a cell population that expresses the α1→2FucT proteins (see, supra, Section 5.2) or immobilized, for example on a substrate or planar surface or in liposomes, micelles, microparticles, or microcapsules, etc.

According to one embodiment of the present invention, the α1→2FucT protein (or a catalytic derivative or analog thereof) can be used in the preparative synthesis of a molecule which comprises a Fucα1→2Galβ1→3GalNAc moiety, said method comprising contacting isolated or purified rat α1→2FucT of the invention with GDP-fucose and a molecule having a terminal Galβ1→3GalNAc moiety for a time sufficient to permit the rat α1→2FucT to transfer the fucose to said molecule and recovering a molecule which comprises Fucα1→2 Galβ1→3GalNAc. In one mode of this embodiment, the molecule having a terminal Galβ1→3GalNAc moiety is a glycolipid, a glycoprotein, a glycolipoprotein or an oligo- or polysaccharide. The oligo- or polysaccharide can be a free saccharide or can be an saccharide immobilized, for example by means of a linker moiety to a substrate or surface. A free saccharide having a Fucα1→2 Galβ1→3GalNAc moiety can be obtained by cleavage of the linker moiety.

According to an alternative embodiment of the present invention, a cell fraction having catalytic activity of α1→2FucT protein (or a catalytic derivative or analog thereof) can be used in the preparative synthesis of a molecule which comprises a Fucα1→2 Galβ1→3GalNAc moiety, said method comprising contacting a cell fraction having rat α1→2FucT of the invention with GDP-fucose and a molecule having a terminal Galβ1→3GalNAc moiety for a time sufficient to permit the rat α1→2FucT to transfer the fucose to said molecule and recovering a molecule which comprises Fucα1→2 Galβ1→3GalNAc. In one mode of this embodiment, the molecule having a terminal Galβ1→3GalNAc moiety is a glycolipid, a glycoprotein, a glycolipoprotein or an oligo- or polysaccharide. The oligo- or polysaccharide can be a free saccharide or can be a saccharide immobilized, for example by means of a linker moiety to a substrate or surface. A free saccharide having a Fucα1→2Galβ1→3GalNAc moiety can be obtained by cleavage of the linker moiety.

According to a specific embodiment, the α1→2FucT (or a catalytic derivative or analog thereof) is used for the preparative synthesis of fucosyl-$GM_1$. In one non-limiting example of this specific embodiment, fucosyl-$GM_1$ is prepared as follows: a reaction mixture composed of 25 μmol of HEPES buffer, pH 7.2, 10 μmol of $MnCl_2$, 500 μg CHAPSO, 0.5 mg $GM_1$ is contacted with a crude cell homogenate of COS-7 cells transiently transfected with plasmid containing the rat α1→2fucosyltransferase coding sequence. Progress of the reaction can be followed with time by withdrawing aliquots of the reaction mixture and spotting it on an HPTLC plate. The plate is then developed in a solvent system composed of $CHCl_3:CH_3OH:H_2O$, 60:40:9, containing 0.02% $CaCl_2$. Glycolipid bands are determined by orcinol spray. Fucosyl-$GM_1$ is recovered.

5.9.3.1. Uses of Saccharide Compositions Produced by α1→2FucT

The glycoproteins, glycolipids, glycolipoproteins or free oligo- or polysaccharides containing a Fucα1→2 Galβ1→3GalNAc moiety produced by α1→2FucT possess nutritional value, and as such may be used as food additives for e.g. infant formula or geriatric formula.

5.9.3.2. Use of Fucosyl-$GM_1$ as an Immunosuppressive or Immunotherapeutic

Fucosyl-$GM_1$ is a cell surface antigen present on a variety of tumors. Thus, fucosyl-$GM_1$ can serve as a vaccine when presented to the immune system of an individual with a tumor expressing this antigen by methods known to those skilled in the art. In one embodiment, fucosyl-$GM_1$ prepared is injected directly into the bloodstream of the individual, where it will elicit an immune response, resulting in the production of antibodies by B-cells against fucosyl-$GM_1$, which antibodies will recognize cells of the tumor. In another embodiment, dendritic cells are extracted from an individual (e.g. by fluorescent activated cell sorting (FACS) using an antibody against a cell surface antigen of dendritic cells as described in U.S. Pat. No. 5,876,917). Preferably, the dendritic cells are induced to proliferate in vitro (e.g. by the method of U.S. Pat. No. 5,851,756). The dendritic cells, whether having been induced to proliferate in vitro or not, are then exposed to fucosyl-$GM_1$. These cells engulf the fucosyl-$GM_1$ antigen and present it on their cell surfaces. After re-introducing the fucosyl-$GM_1$-presenting cells into the patient, either into the bloodstream or locally at the site of the tumor, the cells will stimulate an immune response by activating T-cells, again resulting in the production of anti-tumor antibodies and/or a cytotoxic cellular T-cell immune response against the tumor. Alternatively, the dendritic cells exposed to fucosyl-$GM_1$ can be used in vitro to stimulate T-cells of the individual which T-cells can then be administered to the patient to afford a cellular immune response.

The present invention is further illustrated by the following non-limiting examples.

6. EXAMPLE: CLONING AND EXPRESSION OF THE CATALYTIC DOMAIN OF RAT HEPATOMA GDP-FUCOSE;$GM_1$ α1→2FUCOSYLTRANSFERASE

This example illustrates the cloning and expression of the catalytic domain from rat hepatoma H35 cell GDP-fucose: $GM_1$ α1→2fucosyltransferase, an enzyme which is activated during early stages of chemical carcinogenesis in rat liver.

We have prepared primers based upon consensus sequences of highly conserved regions of the α1→2FucT gene and, using an RT-PCR approach, amplified a product from H35 cell total RNA. These results have indicated that H35 cells encode a novel enzyme, a portion of the 3' end of which has previously been cloned from rat colonic adenocarcinoma PROb cells (Piau, J. -P., et al., 1994, Biochem. J. 300:623–626). Using this information and additional primers from the more 5' end of the gene, we have cloned and expressed a 353 amino acid enzyme construct from H35 cell total RNA with α1→2fucosyltransferase enzyme activity.

6.1. Materials

Rat hepatoma H35 cells and simian COS-7 cells were obtained from the American Type Cell Collection (Manassas, Va.). RNAzol B total RNA isolation kit was obtained from Tel-Test, Inc. (Friendswood, Tex.). Plasmids pZErO-1 and pCR 2.1-TOPO were from Invitrogen (San Diego, Calif.) and pPROTA was received from Dr. Bruce Macher (San Francisco State Univ., San Francisco, Calif.). Rabbit IgG-agarose beads and DEAE-dextran were obtained from Sigma (St. Louis, Mo.). PCR primers were made on a Beckman Oligo 1000 synthesizer. GDP-[$^{14}$C]fucose and [α-$^{35}$S]dATP were obtained from Dupont NEN (Boston, Mass.). Non-automated DNA sequencing was done using the Sequenase Version 2.0 DNA sequencing kit from United States Biochemical Corp. (Cleveland, Ohio) or the SequiTherm EXCEL II DNA sequencing kit from Epicentre Technologies (Madison, Wis.). All other reagents were of the highest quality commercially available.

6.2. Methods 6.2.1. Cell Culture

Rat hepatoma H35 cells and simian COS-7 cells were grown in tissue culture plates in Dulbecco's modified Eagle's medium (DME), supplemented with 10% fetal calf serum. The cells were harvested and passed 1:4 every 5–6 days.

6.2.2. RT-PCR Analysis of Rat Hepatoma H35 Cells: α1→2Fucosyltransferase

Total RNA was extracted from approximately $1\times10^7$ rat hepatoma H35 cells or from 300 mg of F344 whole liver tissue using the RNAzol B method (Tel-test, Inc.). The isolated RNA, in 10 mM Tris buffer, pH 7.5, was initially amplified by RT-PCR using the following primers: primer I (forward), 5'-GGCCGCTTTGGGAACCAGATGG-3' (22-mer) (SEQ ID NO:1); primer II (reverse), 5'-GGTTACACTGCGTGAGCAGCGC-3' (22-mer)(SEQ ID NO:2). These primers were based upon the consensus of portions of human, rabbit and rat intestine α1→2FT coding sequences which have substantial sequence homology. The location of these primers in relation to DNA sequences of other α1→2 FucT enzymes is illustrated in FIG. 1.

cDNA was made from (~1.75 μg total) RNA using random hexamers as primers for MuLV reverse transcriptase. Amplification was then conducted with AmpliTaq DNA polymerase using 200 pM of each of the above primers in 35 cycles of 95° C. for 30 s, 58° C. for 30 s, and 72° C. for 1 min in a Coy thermocycler using a Gene Amp PCR kit (Perkin-Elmer, Branchburg, N.J.) to obtain a PCR product of approximately 0.6-kb.

Some DNA sequence was obtained using the Sequenase PCR product sequencing kit (USB/Amersham, Cleveland, Ohio) for direct sequencing of PCR products using the dideoxy chain termination method (Sanger, F., et al., 1977, Proc. Natl. Acad. Sci. USA). The ~0.6-kb rat PCR product was also cloned into the EcoRV site of pZErO plasmid (Invitrogen) and sequenced using the Sequenase version 2.0 sequencing kit (USB/Amersham) in order to determine the sequence near the 5' and 3' ends of the product.

Based upon sequencing results, which revealed 99% identity between 197 nucleotides at the 3' end of the 0.6-kb PCR product and the 5' end of the rat α1→2FTB reported earlier (Piau, J. -P., et al., 1994, Biochem. J. 300:623–626), a second reverse primer was also made, which is homologous with the 3' end of the coding portion of the rat FTB gene with stop codon (shown in bold lettering below) and some 3' untranslated sequence: primer III (reverse), 5'-TTCCCATCAGAAGGCTCTTCCTGC-3' (SEQ ID NO:3). A second, more upstream forward primer was made based upon rabbit RFT-III, which was found to be the most homologous gene on the nucleotide level to our rat PCR product. This 17-base-pair primer encompassed nucleotides 62–78 of rabbit RFT-III, within the region determined to be near the end of the hydrophobic transmembrane domain of the enzyme. Although sequence homology between differing α1→2FucT genes is considerably reduced in this region compared to more 3' sequences, this particular short sequence showed a reasonable degree of homology to aligned regions of rabbit RFT-II (nucleotides 71–87) and human Sec2 (nucleotides 29–45) genes as well (see FIG. 1). This primer was as follows:

primer IV(forward), 5'-CCGCCTCCACCATCTTC-3' (SEQ ID NO:4). RT-PCR was conducted on total rat H35 cell RNA as described above to obtain a PCR product of approximately 1.1 kb which was cloned into pCR 2.1-TOPO vector and sequenced. A final forward primer was made reflecting exclusively the H35 α1→2FucT gene sequence and adaptors for cloning into the pPROTA fusion protein expression vector: primer V (forward), 5'-ATgaattcCCTCCAGCAGCGAATA-3' (SEQ ID NO:5). An EcoRI site (shown in lower case above) and an additional C residue (bold) were included in the forward primer for in frame cloning into pPROTA (Henion et al., 1994, Glycobiology 4:193–202).

6.2.3. Construction of a Rat α1→2FucT Expression Vector and Expression of RT-PCR cDNA RT-PCR was performed on rat H35 cell total RNA using primer combinations III (SEQ ID NO:3) and V (SEQ ID NO:5), as described above, to obtain a 1.077-kb PCR product, which was then subcloned into pCR 2.1-TOPO. The insert was excised with EcoRI and subsequently cloned into the EcoRI site of pPROTA plasmid for the production of the Protein A-IgG binding domain/rat H35 cell α1→2FucT fusion protein (Henion, T. R., et al., 1994, Glycobiology 4:193–202). Correct orientation of the PCR insert was established by HindIII StuI digestion and the resultant construct named CAT-RFT-pPROTA. CAT-RFT-pPROTA was transiently transfected into COS-7 cells by the DEAE-dextran method (Ausubel, F. M., et al., 1993, Current Protocols in Molecular Biology, Wiley, N.Y.). Secreted fusion protein was purified from the conditioned medium of cells after 4–5 days on IgG-agarose beads as previously described (Holmes, E. H., et al., 1995, J. Biol. Chem. 270:8145–8151) for the assay of α1→2FucT expression.

6.2.4. α1→2Fucosyltransferase Assays

α1→2Fucosyltransferase activity was determined in reaction mixtures containing 2.5 μmol of HEPES buffer, pH7.2, 30 μg of $GM_1$ ganglioside or $nLc_4$, 250 μg phosphatidylglycerol, 1 μmol of $MnCl_2$, 0.5 μmol of CDP-choline, 15 nmol of GDP-[$^{14}$C]fucose (15,000 cpm/nmol), and pPROTA-expressed enzyme bound to IgG-agarose beads in a total volume of 0.1 ml. The reaction mixtures were incubated for 2 h at 37° C., terminated by the addition of 0.1 ml of $CHCl_3$:$CH_3OH$ (2:1), and streaked onto a 4-cm-wide strip of Whatman 3 paper and developed with water overnight. The papers were dried and the labeled product extracted from the origins with 2- to 5-ml washes of $CHCl_3$:$CH_3OH$:$H_2O$ (10:5:1). The combined eluates were concentrated to dryness by an $N_2$ stream and dissolved in 20 μl of $CHCl_3$:$CH_3OH$ (2:1). A 10-μl aliquot of each was spotted onto a HP-TLC plate (Merck)and developed in a solvent system composed of $CHCl_3$:$CH_3OH$:$H_2O$ (60:40:9), 0.02% $CaCl_2.2H_2O$. The radioactive products were located by autoradiography.

6.3. Results 6.3.1. RT-PCR Analysis of α1→2FucT Expression in Rat Hepatoma H35 Cells A survey of aligned nucleotide sequences for human and rabbit α1→2FucT enzyme genes indicates areas where very high sequence homology exists between all forms. Portions of these aligned sequences are shown in FIG. 1. Two of these regions were selected for PCR primer design and initial RT-PCR amplification of H35 cell total RNA. The location of these regions (designated primers I and II; SEQ ID NOS.:1 and 2), corresponding to nucleotides 220 to 241 and 838 to 859 of the rabbit RFT-III for comparison, are also shown in FIG. 1.

A single PCR product slightly over 0.6-kb in size was obtained using primers I (SEQ ID NO:1) and II (SEQ ID NO:2) (FIG. 2, lane 1), which corresponds to the expected fragment size based upon location of these primer regions in the gene. Sequencing on both strands revealed a run of 597 unambiguous nucleotides between the two primer sequences, which were compared to rabbit and rat α1→2FTs. Up to 84% homology in nucleotide sequence was detected between this rat PCR product and the rabbit gene (s). The last 197 nucleotides at the 3' of the PCR product were found to have 99% identity with the 5' end of the rat α1→2FTB fragment reported earlier (Piau, J. -P., et al., 1994, Biochem. J. 300:623–626). The difference (GTG) was detected at the codon for amino acid 50 encoded by the rat FTB fragment (GGT) and was confirmed on two PCR clones with 3 different primers. This represents an amino acid change of glycine in FTB to valine in the H35 cell α1→2FucT at that site. No RT-PCR product was obtained from H35 cell total RNA corresponding to rat FTA (Piau, J. -P., et al., 1994, Biochem. J. 300:623–626) using rat FTA primers (results not shown).

To verify that sequences from the rat FTB fragment constituted the 3' region of the H35 cell α1→2FucT gene, a second RT-PCR experiment was performed using primers I (forward) (SEQ ID NO:1) and III (reverse) (SEQ ID NO:3) (see, supra, Sections 6.1 and 6.2). These primers reflect the start site used in generating the first PCR product through the end of the gene based upon the FTB sequence. As shown in FIG. 2, lane 2, a product, approximately 0.9 kb in size, was obtained from rat H35 total RNA. This PCR product was sequenced and confirmed that rat FTB most probably corresponds to the 3' portion of this gene.

In general, mammalian membrane-bound glycosyltransferases are composed of a short intracellular N-terminal domain, a transmembrane domain, and an extracellular stem region and C-terminal catalytic domain. The stem region corresponds to portions of the extracellular domain which can be removed and are not required for catalytic activity. Generally, most sequence homology among α1→2FucT enzymes occur in the catalytic domain with much lower homology found in DNA sequences corresponding to the more N-terminal portion of the protein. To obtain an RT-PCR product from H35 cell total RNA containing sequences for as much of the N-terminal of the protein as possible to ensure an active enzyme would later be expressed, a forward primer (primer IV; SEQ ID NO:4) corresponding to portions of the transmembrane domain of rabbit RFT-III (nucleotides 62 to 78) where reasonable sequence homology exists between enzymes was used in combination with primer III (SEQ ID NO:3). The results (not shown) indicated that a PCR product of approximately 1.1 kb was generated. Sequencing of this product confirmed that it contained the same sequence obtained in the earlier RT-PCR experiments and included an additional 181 nucleotides of rat H35 cell α1→2FucT sequence at the 5' end.

To obtain a cDNA containing only confirmed rat α1→2FucT sequences for insertion into the EcoRI site of the pPROTA expression vector, a forward primer (primer V; SEQ ID NO:5) was used in combination with primer III (SEQ ID NO:3) in an RT-PCR experiment. Primer V (SEQ ID NO:5) corresponded to the most 5' end of the confirmed rat sequence and contained an adaptor for EcoRI cloning and an extra C residue for in-frame cloning into the pPROTA vector. A product of approximately 1.1 kb (1068 nucleotides of confirmed rat H35 cell α1→2FucT sequence) was amplified from rat H35 cell total RNA using primers V and III (FIG. 2, lane 3). This product represents the majority of the rat H35 cell α1→2FucT, but is missing the start of the coding sequence encoding intracellular and transmembrane domains of the protein. This PCR product was fully sequenced (FIG. 3A) and determined to encode the α1→2FucT associated with malignant transformation in rat liver cells.

Sequence analysis using the BLAST algorithm (Altschul et al., 1990, J. Mol. Biol. 215(3):403–10) determined that the observed sequence is highly homologous to the sequences of all presently known α1→2FucT coding sequences from human, rabbit and rat. It is also virtually identical to the 5' 480 nucleotides of the fragment from rat FTB isolated by Piau et al. (1994, Biochem. J. 300:623–626), which encodes a polypeptide comprising approximately half of the α1→2FucT catalytic domain and possessing no catalytic activity. The sequence shown in FIG. 3A codes for 353 amino acids and contains four potential N-linked glycosylation sites. Table I shows the comparative extent of nucleotide and deduced amino acid sequence from all known enzyme forms. As indicated, high homology was detected between the amino acid sequences of the human Sec2 enzyme and the rat H35 cell α1→2FucT enzyme at 77%. FIG. 3B shows an aligned deduced amino acid sequence comparison between these two enzymes. Rabbit RFT-II and RFT-III enzymes also show a high degree of homology at 71% and 68%, respectively, and rat FTA fragment at 70%. There is far less sequence homology between the rat H35 cell α1→2FucT and the human H and the rabbit RFT-I enzymes. Thus, this new rat enzyme appears to be more closely related to the secretor enzyme than the H enzyme. This is consistent with published results (Larsen, R. D., et al., 1990, Proc. Natl. Acad. Sci. USA 87:6674–6678; Kelly, R. J., et al., 1995, J. Biol. Chem. 270:4640–4649; Hitoshi, S., et al., 1995, J. Biol. Chem. 270:8844–8850; Hitoshi, S., et al., 1996, J. Biol. Chem. 271:16975–16981) which show a proportionally higher specificity for $GM_1$ acceptors compared to lacto- or neolacto-series acceptors for secretor enzyme-like forms compared to the H enzyme.

TABLE I

Comparison of Percent Homology of the Catalytic Domain of Rat Hepatoma H35 Cell α1 → 2FucT with Other Cloned α1 → 2FucT Enzyme Sequences

| | % Homology[1] based on | |
|---|---|---|
| Enzyme | Nucleotide Sequence | Deduced Amino Acid Sequence |
| Human H | 62 | 58 |
| Human Sec2 | 73 | 77 |
| Human Sec1 | 69 | 66 |
| Rabbit FT-I | 64 | 59 |
| Rabbit FT-II | 71 | 71 |
| Rabbit FT-III | 75 | 68 |
| Rat FTA | 69 | 70 |
| Rat FTB | 99 | 99 |

[1]The percentages in the table reflect the degree of homology in the nucleotide stretches representing the overlap between rat $GM_1$-specific α1 → 2FucT and the other α1 → 2FucT sequences. Sequences outside the overlap are not taken into consideration when calculating the homology percentages.

6.3.2. Analysis of pPROTA-Expressed H35 Cell α1→2FucT Activity

Expression of CAT-RFT-pPROTA results in the production of a fusion protein composed of the protein A-IgG-binding domain and the α1→2FucT sequence (SEQ ID NO:10) shown in FIG. 3A. The expressed protein is conveniently isolated by binding to IgG-agarose beads which can be directly assayed for enzyme activity. As shown in FIG. 4, lane 1, the expressed H35 cell α1→2FucT was found to transfer fucose to $GM_1$. No detectable transfer was observed to the neolacto-series acceptor $nLcOse_4Cer$ (lane 3), whose carbohydrate moiety is characterized by a terminal Galβ1→4GlcNAcβ1 saccharide. Further, no transfer to $GM_1$ was observed with beaded enzyme obtained after inserting the H35 cell α1→2FucT cDNA into pPROTA in the reverse orientation (lane 2).

6.4. Discussion

Aligned sequences of human and rabbit α1→2FucT's demonstrate considerable homology in regions corresponding to the catalytic domain of the enzyme. According to the present invention, an RT-PCR cloning strategy utilizing primers corresponding to consensus sequences between these genes was successful in amplifying the appropriate coding sequence from rat H35 cell total RNA. The results demonstrate that this approach provided a significant portion of the H35 cell α1→2FucT sequence. The initial PCR sequence which was illustrated in FIG. 3A overlapped with that from the previously published rat FTB fragment (Piau, J. -P., et al., 1994, Biochem. J. 300:623–626). The rat FTB sequence, when placed in tandem with our upstream sequence, yielded a coding sequence for 292 amino acids and a stop codon. Subsequent use of a primer encompassing the sequence surrounding this stop codon, as well as another encoding a portion of the transmembrane domain of rabbit RFT-III, yielded a cDNA encoding the extracellular portion of the rat H35 cell α1→2FucT. The cDNA corresponding to confirmed rat α1→2FucT sequences when expressed in the pPROTA vector yielded a protein A-IgG-binding domain fusion protein with $GM_1$-specific cα1→2FucT activity.

The observed cDNA sequence of the H35 cell α1→2FucT was found to be distinct yet highly homologous to relevant portions of the genes from other species (Larsen, R. D., et al., 1990, Proc. Natl. Acad. Sci. USA 87:6674–6678; Kelly, R. J., et al., 1995, J. Biol. Chem. 270:4640–4649; Hitoshi, S., et al., 1995, J. Biol. Chem. 270:8844–8850; Hitoshi, S., et al., 1996, J. Biol. Chem. 271:16975–16981; Piau, J. -P., et al., 1994, Biochem. J. 300:623–626). As indicated above, the H35 cell α1→2FucT cDNA obtained is missing 5' regions of the gene encoding the intracellular and transmembrane domains of the enzyme, corresponding to an estimated 15 to 30 amino acids from the N-terminal of the protein based upon sequence alignments with cloned full length proteins. In general, this region has a lower degree of sequence homology in comparison with other α1→2FucT's. Thus, the degree of homology contained within only the extracellular domain may be slightly higher than if the entire coding sequences are compared.

The results indicate that repeated RT-PCR experiments with several primers provided cDNA products with clear, unambiguous, and identical sequences. There was no evidence suggesting multiple PCR products were generated with any primer combination used. In particular, no sequence corresponding to the rat FTA gene (Piau, J. -P., et al., 1994, Biochem. J. 300:623–626) was obtained, even when primers specific for FTA were used. Thus, rat hepatoma H3 5 cells most probably express only a single α1→2FucT enzyme, one with very high specificity for ganglio-series acceptors.

7. EXAMPLE: CLONING AND EXPRESSION OF FULL LENGTH GPD-FUCOSE: $GM_1$α1→2FucT

7.1. Cloning

We have cloned the entire coding region of the rat α1→2FucT gene. Based upon information obtained from a 2984 bp *Rattus norvegicus* FTB mRNA sequence found in GenBank databases (Koda, Y., Submitted to the DDBJ/EMBL/GenBank databases, 1997, Accession #AB006138), a forward primer was designed from the putative start of translation, determined by the rules of Kozak (Kozak, M., 1992, Ann. Rev. Cell Biol. 8:197–225). This mRNA was found to contain 213 nucleotides of upstream untranslated sequence and over 1580 bp of 3' untranslated sequence. As it is reported in the GenBank database, this particular sequence has an error at amino acid 354 (A→H) immediately followed by a nonsense mutation (TAA) for premature termination and therefore, would not express an active enzyme. In addition to the amino acid 354 (A→H) change, this sequence (as reported) is missing 26 crucial amino acids at the C terminus. These are: LTPACPRSHFHLKAKGVTCYVAGRAF (amino acids 355–380 of SEQ ID NO:8). However, based on correct sequence information at the 5' end, a new forward primer was designed:
Primer VI: 5'GCCATGGCCAGCGCCCAGGTTCCT 3' (SEQ ID NO:6). This primer was used in conjunction with Primer III (SEQ ID NO:3), described above, to RT-PCR the entire 1140 bp α1→2FucT coding region (results not shown). This PCR product was sequenced (FIG. 5) and determined to be the nucleotide sequence encoding the α1→2FucT associated with malignant transformation in rat liver cells. Table II shows the comparative extent of nucleotide and deduced amino acid sequence from all known enzyme forms. Full length α1→2FucT cDNA was then cloned into pcDNA3 vector (Invitrogen) in both the positive (FL-RFT-pcDNA3) and negative (FL-RFT(-)-pcDNA3) orientations for later α1→2FucT enzyme assays.

TABLE II

Comparison of Percent Homology of the Full Length Rat Hepatoma H35 Cell α1 → 2FucT with Other Cloned α1 → 2FucT Enzyme Sequences

| | % Homology[1] based on | |
|---|---|---|
| Enzyme | Nucleotide Sequence | Deduced Amino Acid Sequence |
| Human H | 62 | 55 |
| Human Sec2 | 74 | 77 |
| Human Sec1 | 70 | 63 |
| Rabbit FT-I | 64 | 56 |
| Rabbit FT-II | 71 | 67 |
| Rabbit FT-III | 75 | 65 |
| Rat FTA | 69 | 70 |
| Rat FTB | 99 | 99 |

[1]The percentages in the table reflect the degree of homology in the nucleotide stretches representing the overlap between rat $GM_1$-specific α1 → 2FucT and the other α1 → 2FucT sequences. Sequences outside the overlap are not taken into consideration when calculating the homology percentages.

7.2. Analysis of Expressed Full Length α1→2FucT Activity

Expression of full length α1→2FucT cDNA in transfected cells results in membrane-bound enzyme. COS-7 cells were transiently transfected by the DEAE-dextran method (Ausubel, F. M., et al., Current Protocols in Molecular Biology, Wiley, N.Y.) with either FL-RFT-pcDNA3 or FL-RFT(-)-pcDNA3. Four to five days later, the cells were harvested, sonicated in HEPES, glycerol, DTE buffer and assayed for enzyme activity as described previously (Sherwood, A. L., et al., 1998, Arch. Biochem. Biophys. 355:215–221).

As shown in FIG. 6, the expressed recombinant full length enzyme transfers fucose to $GM_1$ with high efficiency; much higher than the pPROTA-expressed truncated enzyme. Comparable transfer was observed in the presence or absence of CHAPSO detergent (100 µg); (lanes D and A, respectively). Somewhat less transfer to $GM_1$ was observed in the presence of 250 µg of phosphatidylglycerol (lane B) and significantly less transfer was observed in the presence of both phosphatiylglycerol (250 µg) and G3634A detergent (100 µg) (Lane C). No fucose transfer was observed under any of these conditions in homogenates from COS-7 cells transfected with FL-RFT(-)-pcDNA3 (results not shown).

8. EXAMPLE: RT-PCR OF α1→2FucT IN RAT LIVER AFTER ADMINISTRATION OF A CARCINOGEN

Expression of α1→2FucT in F344 rat liver before and after administration of the carcinogen 0.03% N-2-acetylaminofluorene (AAF) in the diet (Holmes, E. H., 1990, Carcinogenesis 11:89–94) was tested by RT-PCR of total RNA using primers I and II and compared to the results with H35 cell total RNA. Total RNA was extracted from approximately 200 mg of normal, healthy Fisher 344 rat liver tissue and 200 mg of liver tissue from rats fed a diet containing 0.03% AAF for >3 weeks using the RNAzol B method (Tel-test, Inc., Friendswood, Tex.). RT-PCR was conducted as described (Sherwood, A. L., et al., 1998, Arch. Biochem. Biophys. 355:215–221), with 200 pM of primers I and II which have been found to reproducibly yield a single PCR product of approximately 0.6-kb. This represents a portion of the GDP-fucose:$GM_1$ specific α1→2FucT present in rat hepatoma H35 cells. Results are shown in FIG. 7.

As shown in FIG. 7, an approximately 0.6-kb product corresponding to that derived from H35 cell total RNA (lane 1) was obtained with total RNA derived from liver after 0.03% AAF feeding (lane 3). No PCR product was obtained in the same experiment from total RNA isolated from normal F344 liver (lane 2). The AAF-fed rat liver sample chosen for this study was one of several which displayed a moderate level of α1→2FucT enzyme activity following a feeding regimen of AAF carcinogen. An identical PCR product was also obtained in a later experiment using a second AAF-fed rat liver sample, which had previously been found to display low to moderate α1→2FucT enzyme activity (results not shown). No α1→2FucT enzyme activity has ever been detected in normal liver tissue from rats fed a standard diet lacking AAF. The results presented in FIG. 7 clearly demonstrate that mRNA encoding the α1→2FucT gene is not expressed in normal F344 rat liver tissue but is present in liver tissue after administration of 0.03% AAF. The observation that both enzyme activity and mRNA specific for α1→2FucT is present after only three or more weeks of exposure to AAF confirms that this enzyme is induced in the early stages of chemical carcinogenesis in rat liver.

The observation of the induction of synthesis of this enzyme during very early stages of chemical carcinogenesis suggests that it is an interesting marker for studying this process in vivo. Results presented confirm that mRNA encoding the α1→2FucT gene is not expressed in normal F344 rat liver tissue but is present in liver tissue after administration of 0.03% N-2-acetylaminofluorene.

9. EXAMPLE: INHIBITION OF α1→2FucT ACTIVITY BY ANTISENSE TREATMENT

The ability of antisense α1→2FucT nucleotides to inhibit α1→2FucT activity was assessed in COS-7 cells in which a constant "dose" (1 µg) of FL-RFT-pcDNA3 sense cDNA was transiently transfected with increasing "doses" (1, 2, 3 and 5 µg) of FL-RFT(−)-pcDNA3 antisense cDNA and varying amounts of pcDNA3 vector (no insert) in each case to maintain equi-molar ratios of total plasmid transfected into cells under each condition. Four to five days later, COS-7 cells were harvested, sonicated in HEPES, glycerol, DTE buffer and assayed for α1→2FucT activity as previously described (Sherwood, A. L., et al., 1998, Arch. Biochem. Biophys. 355:215–221). A progressive decrease in enzyme activity was observed with increasing concentrations of antisense α1→2FucT cDNA (FIG. 8). We chose to initially test this system in COS-7 cells because we have had consistently excellent (and rapid) results expressing constructs of various human α1→3fucosyltransferase genes (as well as rat α1→2FucT constructs) in this line. We currently have FL-RFT(−)-pcDNA3 stably transfected H35 hepatoma cells undergoing selection in G418 medium. Our results demonstrate a highly effective antisense treatment system for the down-regulation of rat α1→2FucT.

10. EXAMPLE: PREPARATIVE IN VITRO BIOSYNTHESIS OF FUCOSYL-GM$_1$ UTILIZING RECOMBINANT RAT α1→2FUCOSCYLTRANSFERASE

Preparative biosynthesis of fucosyl-GM$_1$ was conducted in reaction mixtures composed of 25 µmol of HEPES buffer, pH 7.2, 10 µmol of MnCl2, 500 µg CHAPSO, 0.5 mg GM$_1$, and 2 mg crude cell homogenate of COS-7 cells transiently transfected with plasmid containing the entire rat α1→2fucosyltransferase coding sequence in a total volume of 0.5 ml. Progress of the reaction was followed with time by withdrawing 2 µl of the reaction mixture and spotting it on an HPTLC plate. The plate was developed in a solvent system composed of $CHCL_3:CH_3OH:H_2O$, 60:40:9, containing 0.02% $CaCl_2$. Glycolipid bands were determined by orcinol spray (FIG. 9).

The results demonstrate the appearance of increasing amounts of a slower migrating band corresponding to fucosyl-GM$_1$ from transfer of fucose in the α1→2-linkage to the added GM$_1$ acceptor with time. The enzyme is very active yielding almost complete conversion to fucosyl-GM$_1$ after 24 to 48 hours. This preparative biosynthesis can be scaled appropriately to provide any amount of fucosyl-GM$_1$ product needed and is advantageously useful for commercial scale production of fucosyl-GM$_1$.

11. DEPOSIT OF MICROORGANISMS

The following microorganisms were deposited with the American Type Culture Collection (ATCC), 10801 University Blvd., Manassas, Va. on Apr. 22, 1999 and have been assigned accession numbers as indicated.

| Microorganism | Accession Number |
| --- | --- |
| CAT-RFT-pPROTA in E. coli INVα | 207225 |
| FL-RFT-pcDNA3 in E. coli DH5α | 207224 |

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, including patent applications, patents, and publications, the disclosures of which are hereby incorporated by reference in their entireties.

What is claimed is:

1. An isolated protein comprising an amino acid sequence as depicted in FIG. 5 (SEQ ID NO:8).

2. An isolated protein comprising an amino acid sequence as depicted in FIG. 3A (SEQ ID NO:10).

3. An isolated protein consisting of an amino acid sequence as depicted in FIG. 5 (SEQ ID NO:8).

4. An isolated protein consisting of an amino acid sequence as depicted in FIG. 3A (SEQ ID NO:10).

5. An isolated protein, the amino acid sequence of which consists of a catalytic domain defined by amino acids numbers 28–380 as depicted in FIG. 5 (SEQ ID NO:8) or amino acids numbers 1–353 as depicted in FIG. 3A (SEQ ID NO:10).

6. A chimeric protein comprising the protein of claim 3 fused by a covalent bond to at least a portion of a second protein, which second protein is not said protein defined by the sequence as depicted in FIG. 5 (SEQ ID NO:8).

7. A chimeric protein according to claim 6 wherein the second protein is protein A and which portion is the IgG binding domain.

8. A chimeric protein comprising the protein of claim 4 fused by a covalent bond to at least a portion of a second protein, which second portion is not said protein defined by the sequence as depicted in FIG. 5 (SEQ ID NO:8).

9. A chimeric protein according to claim 8 wherein the second protein is protein A and which portion is the IgG binding domain.

10. A chimeric protein comprising the protein of claim 5 fused by a covalent bond to at least a portion of a second protein, which second protein is not said protein defined by the sequence as depicted in FIG. 5 (SEQ ID NO:8).

11. A chimeric protein according to claim 10, wherein the second protein is protein A and which portion is the IgG binding domain.

* * * * *

SEQUENCE LISTING

<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: primer -continued

```
<400> SEQUENCE: 1
ggccgctttg ggaaccagat gg                                                    22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 2
ggttacactg cgtgagcagc gc                                                    22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 3
ttcccatcag aaggctcttc ctgc                                                  24

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 4
ccgcctccac catcttc                                                          17

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
atgaattccc tccagcagcg aata                                                  24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 6
gccatggcca gcgcccaggt tcct                                                  24

<210> SEQ ID NO 7
<211> LENGTH: 1149
<212> TYPE: DNA
<213> ORGANISM: Rattus norvegicus
<220> FEATURE:
<221> NAME/KEY: CDS
<222> LOCATION: (1)..(1143)

<400> SEQUENCE: 7 atg gcc agc gcc cag gtt cct ttc tcc ttt cct ctg gcc cac ttc ctc            48
Met Ala Ser Ala Gln Val Pro Phe Ser Phe Pro Leu Ala His Phe Leu
 1               5                  10                  15
```

-continued

| | |
|---|---|
| atc ttt gtc ttc gtg act tcc acc atc atc cac ctc cag cag cga ata<br>Ile Phe Val Phe Val Thr Ser Thr Ile Ile His Leu Gln Gln Arg Ile<br>20                        25                    30 | 96 |
| gtg aag ctc caa ccc ctg tca gag aag gaa tta ccg atg acg act caa<br>Val Lys Leu Gln Pro Leu Ser Glu Lys Glu Leu Pro Met Thr Thr Gln<br>       35                    40                    45 | 144 |
| atg tcc tcg gga aac aca gaa agc cca gag atg cga cgg gac agc gag<br>Met Ser Ser Gly Asn Thr Glu Ser Pro Glu Met Arg Arg Asp Ser Glu<br>50                        55                    60 | 192 |
| cag cat ggg aat gga gag ctg cgg ggc atg ttc acg atc aat tcc att<br>Gln His Gly Asn Gly Glu Leu Arg Gly Met Phe Thr Ile Asn Ser Ile<br>65                        70                    75                    80 | 240 |
| ggc cgg ctg ggg aac cag atg ggc gaa tac gcc aca ctc ttt gca ctg<br>Gly Arg Leu Gly Asn Gln Met Gly Glu Tyr Ala Thr Leu Phe Ala Leu<br>       85                    90                    95 | 288 |
| gcc agg atg aac gga cgg ctt gcg ttc atc ccc gca tcc atg cac aac<br>Ala Arg Met Asn Gly Arg Leu Ala Phe Ile Pro Ala Ser Met His Asn<br>            100                    105                110 | 336 |
| gct cta gcg ccc atc ttc agg atc agc ctc ccg gtg tta cac agc gac<br>Ala Leu Ala Pro Ile Phe Arg Ile Ser Leu Pro Val Leu His Ser Asp<br>115                      120                    125 | 384 |
| acg gcc aaa aag atc cca tgg cag aat tac cat ctc aac gac tgg atg<br>Thr Ala Lys Lys Ile Pro Trp Gln Asn Tyr His Leu Asn Asp Trp Met<br>        130                    135                140 | 432 |
| gag gag cgt tac cgc cac att ccg gga cac ttt gtg cgc ttc acg gga<br>Glu Glu Arg Tyr Arg His Ile Pro Gly His Phe Val Arg Phe Thr Gly<br>145                      150                    155                160 | 480 |
| tac ccg tgc tcc tgg acc ttc tac cac cac ctg cgc cca gag atc ctg<br>Tyr Pro Cys Ser Trp Thr Phe Tyr His His Leu Arg Pro Glu Ile Leu<br>                  165                    170                175 | 528 |
| aag gag ttc acc ctg cat gac cac gtg cgg gag gag gcc cag gcc ttc<br>Lys Glu Phe Thr Leu His Asp His Val Arg Glu Glu Ala Gln Ala Phe<br>              180                    185                190 | 576 |
| ctg cgt ggt ctg cgg gtg aat ggg agc cag ccg agt act ttt gtg ggt<br>Leu Arg Gly Leu Arg Val Asn Gly Ser Gln Pro Ser Thr Phe Val Gly<br>195                      200                    205 | 624 |
| gtc cat gtg cgc cga ggg gac tat gtg cat gtc atg cct aat gtg tgg<br>Val His Val Arg Arg Gly Asp Tyr Val His Val Met Pro Asn Val Trp<br>        210                    215                220 | 672 |
| aag ggc gtg gtg gct gac cgg ggt tac ctg gaa aag gcc ctg gat atg<br>Lys Gly Val Val Ala Asp Arg Gly Tyr Leu Glu Lys Ala Leu Asp Met<br>225                      230                    235                240 | 720 |
| ttc cgg gca cgc tat tca tct cca gtc ttc gtg gtt aca agc aac ggt<br>Phe Arg Ala Arg Tyr Ser Ser Pro Val Phe Val Val Thr Ser Asn Gly<br>                245                    250                255 | 768 |
| atg gcc tgg tgc cgg gag aac att aat gct tcc cga gga gac gtg gtg<br>Met Ala Trp Cys Arg Glu Asn Ile Asn Ala Ser Arg Gly Asp Val Val<br>        260                    265                270 | 816 |
| ttc gcg ggc aat ggt att gag ggg tcg cca gcc aag gac ttc gcg ctg<br>Phe Ala Gly Asn Gly Ile Glu Gly Ser Pro Ala Lys Asp Phe Ala Leu<br>275                      280                    285 | 864 |
| ctc acc cag tgc aac cac acc atc atg act att ggg acc ttt ggg att<br>Leu Thr Gln Cys Asn His Thr Ile Met Thr Ile Gly Thr Phe Gly Ile<br>        290                    295                300 | 912 |
| tgg gct gcc tac ctg gca ggt ggt gat acc atc tac tta gcc aac tac<br>Trp Ala Ala Tyr Leu Ala Gly Gly Asp Thr Ile Tyr Leu Ala Asn Tyr<br>305                      310                    315                320 | 960 |
| acc ctt ccg gat tct ccg ttc ctc aaa gtc ttt aag cca gag gca gcc<br>Thr Leu Pro Asp Ser Pro Phe Leu Lys Val Phe Lys Pro Glu Ala Ala<br>                325                    330                335 | 1008 |

-continued

```
ttc cta ccc gaa tgg gtg ggc atc cct gcc gat ctg tcc cca ctc ctt    1056
Phe Leu Pro Glu Trp Val Gly Ile Pro Ala Asp Leu Ser Pro Leu Leu
            340                 345                 350 aag gca tta aca cca gcc tgt cct cgg tcc cac ttc cac ctc aag gca    1104
Lys Ala Leu Thr Pro Ala Cys Pro Arg Ser His Phe His Leu Lys Ala
        355                 360                 365 aaa gga gtc act tgt tac gtc gca gga aga gcc ttc tga tgggaa         1149
Lys Gly Val Thr Cys Tyr Val Ala Gly Arg Ala Phe
    370                 375                 380
```

<210> SEQ ID NO 8
<211> LENGTH: 380
<212> TYPE: PRT
<213> ORGANISM: Rattus norvegicus

<400> SEQUENCE: 8

| | | | | | | | | | | | | | | | |
|---|---|---|---|---|---|---|---|---|---|---|---|---|---|---|---|
| Met | Ala | Ser | Ala | Gln | Val | Pro | Phe | Ser | Phe | Pro | Leu | Ala | His | Phe | Leu |
| 1 | | | | 5 | | | | | 10 | | | | | 15 | |
| Ile | Phe | Val | Phe | Val | Thr | Ser | Thr | Ile | Ile | His | Leu | Gln | Gln | Arg | Ile |
| | | | 20 | | | | | 25 | | | | | 30 | | |
| Val | Lys | Leu | Gln | Pro | Leu | Ser | Glu | Lys | Glu | Leu | Pro | Met | Thr | Thr | Gln |
| | | 35 | | | | | 40 | | | | | 45 | | | |
| Met | Ser | Ser | Gly | Asn | Thr | Glu | Ser | Pro | Glu | Met | Arg | Arg | Asp | Ser | Glu |
| | 50 | | | | | 55 | | | | | 60 | | | | |
| Gln | His | Gly | Asn | Gly | Glu | Leu | Arg | Gly | Met | Phe | Thr | Ile | Asn | Ser | Ile |
| 65 | | | | | 70 | | | | | 75 | | | | | 80 |
| Gly | Arg | Leu | Gly | Asn | Gln | Met | Gly | Glu | Tyr | Ala | Thr | Leu | Phe | Ala | Leu |
| | | | | 85 | | | | | 90 | | | | | 95 | |
| Ala | Arg | Met | Asn | Gly | Arg | Leu | Ala | Phe | Ile | Pro | Ala | Ser | Met | His | Asn |
| | | | 100 | | | | | 105 | | | | | 110 | | |
| Ala | Leu | Ala | Pro | Ile | Phe | Arg | Ile | Ser | Leu | Pro | Val | Leu | His | Ser | Asp |
| | | | 115 | | | | | 120 | | | | | 125 | | |
| Thr | Ala | Lys | Lys | Ile | Pro | Trp | Gln | Asn | Tyr | His | Leu | Asn | Asp | Trp | Met |
| | 130 | | | | | 135 | | | | | 140 | | | | |
| Glu | Glu | Arg | Tyr | Arg | His | Ile | Pro | Gly | His | Phe | Val | Arg | Phe | Thr | Gly |
| 145 | | | | | 150 | | | | | 155 | | | | | 160 |
| Tyr | Pro | Cys | Ser | Trp | Thr | Phe | Tyr | His | His | Leu | Arg | Pro | Glu | Ile | Leu |
| | | | | 165 | | | | | 170 | | | | | 175 | |
| Lys | Glu | Phe | Thr | Leu | His | Asp | His | Val | Arg | Glu | Glu | Ala | Gln | Ala | Phe |
| | | | 180 | | | | | 185 | | | | | 190 | | |
| Leu | Arg | Gly | Leu | Arg | Val | Asn | Gly | Ser | Gln | Pro | Ser | Thr | Phe | Val | Gly |
| | | 195 | | | | | 200 | | | | | 205 | | | |
| Val | His | Val | Arg | Arg | Gly | Asp | Tyr | Val | His | Val | Met | Pro | Asn | Val | Trp |
| | 210 | | | | | 215 | | | | | 220 | | | | |
| Lys | Gly | Val | Val | Ala | Asp | Arg | Gly | Tyr | Leu | Glu | Lys | Ala | Leu | Asp | Met |
| 225 | | | | | 230 | | | | | 235 | | | | | 240 |
| Phe | Arg | Ala | Arg | Tyr | Ser | Ser | Pro | Val | Phe | Val | Val | Thr | Ser | Asn | Gly |
| | | | | 245 | | | | | 250 | | | | | 255 | |
| Met | Ala | Trp | Cys | Arg | Glu | Asn | Ile | Asn | Ala | Ser | Arg | Gly | Asp | Val | Val |
| | | | 260 | | | | | 265 | | | | | 270 | | |
| Phe | Ala | Gly | Asn | Gly | Ile | Glu | Gly | Ser | Pro | Ala | Lys | Asp | Phe | Ala | Leu |
| | | 275 | | | | | 280 | | | | | 285 | | | |
| Leu | Thr | Gln | Cys | Asn | His | Thr | Ile | Met | Thr | Ile | Gly | Thr | Phe | Gly | Ile |
| | 290 | | | | | 295 | | | | | 300 | | | | |
| Trp | Ala | Ala | Tyr | Leu | Ala | Gly | Gly | Asp | Thr | Ile | Tyr | Leu | Ala | Asn | Tyr |

```
              305                 310                 315                 320
Thr Leu Pro Asp Ser Pro Phe Leu Lys Val Phe Lys Pro Glu Ala Ala
                    325                 330                 335

Phe Leu Pro Glu Trp Val Gly Ile Pro Ala Asp Leu Ser Pro Leu Leu
                340                 345                 350

Lys Ala Leu Thr Pro Ala Cys Pro Arg Ser His Phe His Leu Lys Ala
            355                 360                 365

Lys Gly Val Thr Cys Tyr Val Ala Gly Arg Ala Phe
        370                 375                 380

<210> SEQ ID NO 9
<211> LENGTH: 1068
<212> TYPE: DNA
<213> ORGANISM: Rattus norvegicus
<220> FEATURE:
<221> NAME/KEY: CDS
<222> LOCATION: (1)..(1062)

<400> SEQUENCE: 9 ctc cag cag cga ata gtg aag ctc caa ccc ctg tca gag aag gaa tta       48
Leu Gln Gln Arg Ile Val Lys Leu Gln Pro Leu Ser Glu Lys Glu Leu
  1               5                  10                  15 ccg atg acg act caa atg tcc tcg gga aac aca gaa agc cca gag atg       96
Pro Met Thr Thr Gln Met Ser Ser Gly Asn Thr Glu Ser Pro Glu Met
             20                  25                  30 cga cgg gac agc gag cag cat ggg aat gga gag ctg cgg ggc atg ttc      144
Arg Arg Asp Ser Glu Gln His Gly Asn Gly Glu Leu Arg Gly Met Phe
         35                  40                  45 acg atc aat tcc att ggc cgg ctg ggg aac cag atg ggc gaa tac gcc      192
Thr Ile Asn Ser Ile Gly Arg Leu Gly Asn Gln Met Gly Glu Tyr Ala
     50                  55                  60 aca ctc ttt gca ctg gcc agg atg aac gga cgg ctt gcg ttc atc ccc      240
Thr Leu Phe Ala Leu Ala Arg Met Asn Gly Arg Leu Ala Phe Ile Pro
 65                  70                  75                  80 gca tcc atg cac aac gct cta gcg ccc atc ttc agg atc agc ctc ccg      288
Ala Ser Met His Asn Ala Leu Ala Pro Ile Phe Arg Ile Ser Leu Pro
                 85                  90                  95 gtg tta cac agc gac acg gcc aaa aag atc cca tgg cag aat tac cat      336
Val Leu His Ser Asp Thr Ala Lys Lys Ile Pro Trp Gln Asn Tyr His
            100                 105                 110 ctc aac gac tgg atg gag gag cgt tac cgc cac att ccg gga cac ttt      384
Leu Asn Asp Trp Met Glu Glu Arg Tyr Arg His Ile Pro Gly His Phe
        115                 120                 125 gtg cgc ttc acg gga tac ccg tgc tcc tgg acc ttc tac cac cac ctg      432
Val Arg Phe Thr Gly Tyr Pro Cys Ser Trp Thr Phe Tyr His His Leu
    130                 135                 140 cgc cca gag atc ctg aag gag ttc acc ctg cat gac cac gtg cgg gag      480
Arg Pro Glu Ile Leu Lys Glu Phe Thr Leu His Asp His Val Arg Glu
145                 150                 155                 160 gag gcc cag gcc ttc ctg cgt ggt ctg cgg gtg aat ggg agc cag ccg      528
Glu Ala Gln Ala Phe Leu Arg Gly Leu Arg Val Asn Gly Ser Gln Pro
                165                 170                 175 agt act ttt gtg ggt gtc cat gtg cgc cga ggg gac tat gtg cat gtc      576
Ser Thr Phe Val Gly Val His Val Arg Arg Gly Asp Tyr Val His Val
            180                 185                 190 atg cct aat gtg tgg aag ggc gtg gtg gct gac cgg gtt tac ctg gaa      624
Met Pro Asn Val Trp Lys Gly Val Val Ala Asp Arg Val Tyr Leu Glu
        195                 200                 205 aag gcc ctg gat atg ttc cgg gca cgc tat tca tct cca gtc ttc gtg      672
Lys Ala Leu Asp Met Phe Arg Ala Arg Tyr Ser Ser Pro Val Phe Val
    210                 215                 220
```

```
        210                 215                 220
gtt aca agc aac ggt atg gcc tgg tgc cgg gag aac att aat gct tcc    720
Val Thr Ser Asn Gly Met Ala Trp Cys Arg Glu Asn Ile Asn Ala Ser
225                 230                 235                 240 cga gga gac gtg gtg ttc gcg ggc aat ggt att gag ggg tcg cca gcc    768
Arg Gly Asp Val Val Phe Ala Gly Asn Gly Ile Glu Gly Ser Pro Ala
                245                 250                 255 aag gac ttc gcg ctg ctc acc cag tgc aac cac acc atc atg act att    816
Lys Asp Phe Ala Leu Leu Thr Gln Cys Asn His Thr Ile Met Thr Ile
            260                 265                 270 ggg acc ttt ggg att tgg gct gcc tac ctg gca ggt ggt gat acc atc    864
Gly Thr Phe Gly Ile Trp Ala Ala Tyr Leu Ala Gly Gly Asp Thr Ile
        275                 280                 285 tac tta gcc aac tac acc ctt ccg gat tct ccg ttc ctc aaa gtc ttt    912
Tyr Leu Ala Asn Tyr Thr Leu Pro Asp Ser Pro Phe Leu Lys Val Phe
    290                 295                 300 aag cca gag gca gcc ttc cta ccc gaa tgg gtg ggc atc cct gcc gat    960
Lys Pro Glu Ala Ala Phe Leu Pro Glu Trp Val Gly Ile Pro Ala Asp
305                 310                 315                 320 ctg tcc cca ctc ctt aag gca tta aca cca gcc tgt cct cgg tcc cac   1008
Leu Ser Pro Leu Leu Lys Ala Leu Thr Pro Ala Cys Pro Arg Ser His
                325                 330                 335 ttc cac ctc aag gca aaa gga gtc act tgt tac gtc gca gga aga gcc   1056
Phe His Leu Lys Ala Lys Gly Val Thr Cys Tyr Val Ala Gly Arg Ala
            340                 345                 350 ttc tga tgggaa                                                     1068
Phe

<210> SEQ ID NO 10
<211> LENGTH: 353
<212> TYPE: PRT
<213> ORGANISM: Rattus norvegicus

<400> SEQUENCE: 10

Leu Gln Gln Arg Ile Val Lys Leu Gln Pro Leu Ser Glu Lys Glu Leu
 1               5                  10                  15

Pro Met Thr Thr Gln Met Ser Ser Gly Asn Thr Glu Ser Pro Glu Met
                20                  25                  30

Arg Arg Asp Ser Glu Gln His Gly Asn Gly Glu Leu Arg Gly Met Phe
            35                  40                  45

Thr Ile Asn Ser Ile Gly Arg Leu Gly Asn Gln Met Gly Glu Tyr Ala
        50                  55                  60

Thr Leu Phe Ala Leu Ala Arg Met Asn Gly Arg Leu Ala Phe Ile Pro
65                  70                  75                  80

Ala Ser Met His Asn Ala Leu Ala Pro Ile Phe Arg Ile Ser Leu Pro
                85                  90                  95

Val Leu His Ser Asp Thr Ala Lys Lys Ile Pro Trp Gln Asn Tyr His
            100                 105                 110

Leu Asn Asp Trp Met Glu Glu Arg Tyr Arg His Ile Pro Gly His Phe
        115                 120                 125

Val Arg Phe Thr Gly Tyr Pro Cys Ser Trp Thr Phe Tyr His His Leu
    130                 135                 140

Arg Pro Glu Ile Leu Lys Glu Phe Thr Leu His Asp His Val Arg Glu
145                 150                 155                 160

Glu Ala Gln Ala Phe Leu Arg Gly Leu Arg Val Asn Gly Ser Gln Pro
                165                 170                 175

Ser Thr Phe Val Gly Val His Val Arg Arg Gly Asp Tyr Val His Val
```

-continued

```
                180                 185                 190
Met Pro Asn Val Trp Lys Gly Val Ala Asp Arg Gly Tyr Leu Glu
            195                 200                 205

Lys Ala Leu Asp Met Phe Arg Ala Arg Tyr Ser Ser Pro Val Phe Val
210                 215                 220

Val Thr Ser Asn Gly Met Ala Trp Cys Arg Glu Asn Ile Asn Ala Ser
225                 230                 235                 240

Arg Gly Asp Val Val Phe Ala Gly Asn Gly Ile Glu Gly Ser Pro Ala
                245                 250                 255

Lys Asp Phe Ala Leu Leu Thr Gln Cys Asn His Thr Ile Met Thr Ile
                260                 265                 270

Gly Thr Phe Gly Ile Trp Ala Ala Tyr Leu Ala Gly Gly Asp Thr Ile
            275                 280                 285

Tyr Leu Ala Asn Tyr Thr Leu Pro Asp Ser Pro Phe Leu Lys Val Phe
290                 295                 300

Lys Pro Glu Ala Ala Phe Leu Pro Glu Trp Val Gly Ile Pro Ala Asp
305                 310                 315                 320

Leu Ser Pro Leu Leu Lys Ala Leu Thr Pro Ala Cys Pro Arg Ser His
                325                 330                 335

Phe His Leu Lys Ala Lys Gly Val Thr Cys Tyr Val Ala Gly Arg Ala
                340                 345                 350

Phe
```

```
<210> SEQ ID NO 11
<211> LENGTH: 344
<212> TYPE: PRT
<213> ORGANISM: Homo sapiens

<400> SEQUENCE: 11
```

```
Met Leu Val Val Gln Met Pro Phe Ser Phe Pro Met Ala His Phe Ile
1               5                   10                  15

Leu Phe Val Phe Thr Val Ser Thr Ile Phe His Val Gln Gln Arg Leu
                20                  25                  30

Ala Lys Ile Gln Ala Met Trp Glu Leu Pro Val Gln Ile Pro Val Leu
            35                  40                  45

Ala Ser Thr Ser Lys Ala Leu Gly Pro Ser Gln Leu Arg Gly Met Trp
50                  55                  60

Thr Ile Asn Ala Ile Gly Arg Leu Gly Asn Gln Met Gly Glu Tyr Ala
65                  70                  75                  80

Thr Leu Tyr Ala Leu Ala Lys Met Asn Gly Arg Pro Ala Phe Ile Pro
                85                  90                  95

Ala Gln Met His Ser Thr Leu Ala Pro Ile Phe Arg Ile Thr Leu Pro
            100                 105                 110

Val Leu His Ser Ala Thr Ala Ser Arg Ile Pro Trp Gln Asn Tyr His
            115                 120                 125

Leu Asn Asp Trp Met Glu Glu Tyr Arg His Ile Pro Pro Gly Glu
            130                 135                 140

Tyr Val Arg Phe Thr Gly Tyr Pro Cys Ser Trp Thr Phe Tyr His His
145                 150                 155                 160

Leu Arg Gln Glu Ile Leu Gln Glu Phe Thr Leu His Asp His Val Arg
                165                 170                 175

Glu Glu Ala Gln Lys Phe Leu Arg Gly Leu Gln Val Asn Gly Ser Arg
            180                 185                 190

Pro Gly Thr Phe Val Gly Val His Val Arg Arg Gly Asp Tyr Val His
```

```
                    195                 200                 205
Val Met Pro Lys Val Trp Lys Gly Val Val Ala Asp Arg Arg Tyr Leu
        210                 215                 220

Gln Gln Ala Leu Asp Trp Phe Arg Ala Arg Tyr Ser Ser Leu Ile Phe
225                 230                 235                 240

Val Val Thr Ser Asn Gly Met Ala Trp Cys Arg Glu Asn Ile Asp Thr
                245                 250                 255

Ser His Gly Asp Val Val Phe Ala Gly Asp Gly Ile Glu Gly Ser Pro
                260                 265                 270

Ala Lys Asp Phe Ala Leu Leu Thr Gln Cys Asn His Thr Ile Met Thr
            275                 280                 285

Ile Gly Thr Phe Gly Ile Trp Ala Ala Tyr Leu Thr Gly Gly Asp Thr
        290                 295                 300

Ile Tyr Leu Ala Asn Tyr Thr Leu Pro Asp Ser Pro Phe Leu Lys Ile
305                 310                 315                 320

Phe Lys Pro Glu Ala Ala Phe Leu Pro Glu Trp Thr Gly Ile Ala Ala
                325                 330                 335

Asp Leu Ser Pro Leu Leu Lys His
            340
```

```
<210> SEQ ID NO 12
<211> LENGTH: 100
<212> TYPE: DNA
<213> ORGANISM: Homo sapiens

<400> SEQUENCE: 12
tgtcctctct gtaatcttct tcctccatat ccatcaagac agctttccac atggcctagg    60
cctgtcgatc ctgtgtcaag accgccgcct ggtgacaccc                         100

<210> SEQ ID NO 13
<211> LENGTH: 50
<212> TYPE: DNA
<213> ORGANISM: Homo sapiens

<400> SEQUENCE: 13
accccaatgg ccggtttggt aatcagatgg gacagtatgc cacgctgctg               50

<210> SEQ ID NO 14
<211> LENGTH: 100
<212> TYPE: DNA
<213> ORGANISM: Homo sapiens

<400> SEQUENCE: 14
atggacagga ggctacaccg tgaaagact ttgccctgct cacacagtgc aaccacacca     60
ttatgaccat tggcaccttc ggcttctggg ctgcctacct                         100

<210> SEQ ID NO 15
<211> LENGTH: 100
<212> TYPE: DNA
<213> ORGANISM: Homo sapiens

<400> SEQUENCE: 15
catgctggtc gttcagatgc ctttctcctt tcccatggcc cacttcatcc tctttgtctt    60
tacggtttcc actatatttc acgttcagca gcggctagcg                         100

<210> SEQ ID NO 16
<211> LENGTH: 50
<212> TYPE: DNA
```

<213> ORGANISM: Homo sapiens

<400> SEQUENCE: 16
atgcaatagg ccgcctgggg aaccagatgg gcgagtacgc cacactgtac          50

<210> SEQ ID NO 17
<211> LENGTH: 100
<212> TYPE: DNA
<213> ORGANISM: Homo sapiens

<400> SEQUENCE: 17
atggacagga ggctacaccg tggaaagact ttgccctgct cacacagtgc aaccacacca          60
ttatgaccat tggcaccttc ggcttctggg ctgcctacct          100

<210> SEQ ID NO 18
<211> LENGTH: 94
<212> TYPE: DNA
<213> ORGANISM: Homo sapiens

<400> SEQUENCE: 18
ccccacagcc gtcaagggat tctgggccac ccgcccttcc ttctccacct tctacttcgt          60 cttttgccatt tttgtggtgt ccaccatctt tcac          94

<210> SEQ ID NO 19
<211> LENGTH: 50
<212> TYPE: DNA
<213> ORGANISM: Homo sapiens

<400> SEQUENCE: 19
actccaaggg ccgcctgggg aaccagatgg gcgagtacgc cacgctgtac          50

<210> SEQ ID NO 20
<211> LENGTH: 100
<212> TYPE: DNA
<213> ORGANISM: Homo sapiens

<400> SEQUENCE: 20
atggcctcca gggctcacct gccaaggact tcgcactgct cacacagtgc aaccacacca          60
tcatcaccgt gggcaccttc ggggtctggg ccgcgtacct          100

<210> SEQ ID NO 21
<211> LENGTH: 100
<212> TYPE: DNA
<213> ORGANISM: Oryctolagus cuniculus

<400> SEQUENCE: 21
tgccctctct gccttctcct tcctcctgca tctccaccaa gacctctccc gaaacggcct          60
agccctgtct ctcccgtgtc tggaacgcca gccggtgcca          100

<210> SEQ ID NO 22
<211> LENGTH: 50
<212> TYPE: DNA
<213> ORGANISM: Oryctolagus cuniculus

<400> SEQUENCE: 22
acccggatgg ccgctttggg aaccagatgg ggcagtacgc cactctgctc          50

<210> SEQ ID NO 23
<211> LENGTH: 100
<212> TYPE: DNA
<213> ORGANISM: Oryctolagus cuniculus

<400> SEQUENCE: 23
acggcctcga gagctcgccg gccaaggact ttgcgctgct cacgcagtgt aaccacaccg    60
tcatgaccat cggcaccttt ggcttctggg ccgcctacct                         100

<210> SEQ ID NO 24
<211> LENGTH: 94
<212> TYPE: DNA
<213> ORGANISM: Oryctolagus cuniculus

<400> SEQUENCE: 24
tcccacagcc accaggagat tgagggccac ccacccgtcc gtctccacca tctacttcct    60
gttcaccatc tttgtggtat ccactgtctt ccac                               94

<210> SEQ ID NO 25
<211> LENGTH: 50
<212> TYPE: DNA
<213> ORGANISM: Oryctolagus cuniculus

<400> SEQUENCE: 25
acgccatggg ccgcctgggg aaccagatgg gcgagtacgc cacgctgtac                50

<210> SEQ ID NO 26
<211> LENGTH: 100
<212> TYPE: DNA
<213> ORGANISM: Oryctolagus cuniculus

<400> SEQUENCE: 26
acggcctcga gggctctccg gccaaggact ttgcgctgct cacgcagtgt aaccacaccg    60
tcatgaccat cggcaccttt ggcttctggg ccgcctacct                         100

<210> SEQ ID NO 27
<211> LENGTH: 79
<212> TYPE: DNA
<213> ORGANISM: Oryctolagus cuniculus

<400> SEQUENCE: 27
catggtccac gtcatcctct tcgtcttcac cgcctccacc atcttccacc tccagcagcg    60
cctggtgagg attcaaccc                                                79

<210> SEQ ID NO 28
<211> LENGTH: 50
<212> TYPE: DNA
<213> ORGANISM: Oryctolagus cuniculus

<400> SEQUENCE: 28
acgccatggg ccgcctgggg aaccagatgg gcgagtacgc cacgctgtat                50

<210> SEQ ID NO 29
<211> LENGTH: 100
<212> TYPE: DNA
<213> ORGANISM: Oryctolagus cuniculus

<400> SEQUENCE: 29
atggcctcga gagctcgccg gccaaggact ttgcgctgct cacgcaggtt aaccacaccg    60
tcatgaccat cggcaccttt gggatctggg ccgcctacct                         100